(12) United States Patent
Ogawa

(10) Patent No.: US 11,515,034 B2
(45) Date of Patent: Nov. 29, 2022

(54) NURSE CALL SYSTEM

(71) Applicant: Aiphone Co., Ltd., Nagoya (JP)

(72) Inventor: Kenichi Ogawa, Nagoya (JP)

(73) Assignee: Aiphone Co., Ltd., Nagoya (JP)

( * ) Notice: Subject to any disclaimer, the term of this patent is extended or adjusted under 35 U.S.C. 154(b) by 429 days.

(21) Appl. No.: 16/859,159

(22) Filed: Apr. 27, 2020

(65) Prior Publication Data

US 2020/0258619 A1   Aug. 13, 2020

Related U.S. Application Data

(63) Continuation of application No. PCT/JP2018/015903, filed on Apr. 17, 2018.

(30) Foreign Application Priority Data

Nov. 15, 2017 (JP) .............................. JP2017-220234
Feb. 28, 2018 (JP) .............................. JP2018-034649
Mar. 19, 2018 (JP) .............................. JP2018-051336

(51) Int. Cl.
*G08B 1/08* (2006.01)
*G16H 40/20* (2018.01)
(Continued)

(52) U.S. Cl.
CPC ........... *G16H 40/20* (2018.01); *G06Q 20/085* (2013.01); *G08B 5/36* (2013.01); *G16H 40/67* (2018.01);
(Continued)

(58) Field of Classification Search
CPC ...... G16H 40/20; G16H 40/67; G06Q 20/085; G06Q 20/321; G06Q 20/3224;
(Continued)

(56) References Cited

U.S. PATENT DOCUMENTS 5,838,223 A * 11/1998 Gallant ............... G08B 25/009
340/286.07
7,598,853 B2   10/2009 Becker et al.
(Continued)

FOREIGN PATENT DOCUMENTS

CN    101287405 A   10/2008
CN    102984048 A    3/2013
(Continued)

OTHER PUBLICATIONS

International Search Report and Written Opinion (Application No. PCT/JP2018/015903) dated Jun. 19, 2018.
(Continued)

*Primary Examiner* — Toan N Pham
(74) *Attorney, Agent, or Firm* — Burr & Brown, PLLC

(57) ABSTRACT

A nurse call system that enables a call for a nurse from anywhere in a hospital ward while a patient carries a mobile phone is provided. The nurse call system includes a plurality of patient mobile phones 10 are carried by hospitalized patients and connected to a controller 8 via a base station 12 as with nurse mobile phones 9, and each patient mobile phone 10 has a hospital room ID and a nurse call slave device ID registered therein for recognizing a bed location of the patient carrying the patient mobile phone 10, thus enabling a nurse call operation for transmitting a call signal with the hospital room ID and the slave device ID added thereto, to the nurse call master device 7 and at least one of the nurse mobile phones 9, through a predetermined operation.

7 Claims, 20 Drawing Sheets

(51) Int. Cl.
- *G16H 40/67* (2018.01)
- *G06Q 20/08* (2012.01)
- *G08B 5/36* (2006.01)
- *H04M 3/42* (2006.01)
- *H04M 7/00* (2006.01)
- *H04Q 3/62* (2006.01)
- *H04W 84/20* (2009.01)

(52) U.S. Cl.
CPC ....... *H04M 3/42331* (2013.01); *H04M 7/009* (2013.01); *H04Q 3/627* (2013.01); *H04W 84/20* (2013.01); *H04Q 2213/1322* (2013.01); *H04Q 2213/13286* (2013.01)

(58) Field of Classification Search
CPC ........ G06Q 20/3255; G08B 5/36; G08B 3/10; H04M 3/42331; H04M 7/009; H04M 2207/18; H04M 2242/30; H04M 3/42314; H04M 9/02; H04M 3/42348; H04M 9/00; H04Q 3/627; H04Q 2213/1322; H04Q 2213/13286; H04Q 2213/13098; H04Q 3/62; H04W 84/20; A61G 12/00
See application file for complete search history.

(56) References Cited

U.S. PATENT DOCUMENTS

| | | | | |
|---|---|---|---|---|
| 9,937,090 | B2* | 4/2018 | Hayes | G16H 40/20 |
| 2014/0169795 | A1* | 6/2014 | Clough | H04W 88/02 |
| | | | | 398/106 |
| 2017/0116377 | A1* | 4/2017 | Kitagawa | G16H 40/20 |

FOREIGN PATENT DOCUMENTS

| | | |
|---|---|---|
| CN | 106163481 A | 11/2016 |
| CN | 206441294 U | 8/2017 |
| JP | 2002-199115 A1 | 7/2002 |
| JP | 2003-281271 A1 | 10/2003 |
| JP | 2005-236437 A1 | 9/2005 |
| JP | 2005-244775 A1 | 9/2005 |
| JP | 2007-124312 A1 | 5/2007 |
| JP | 2008-293301 A1 | 12/2008 |
| JP | 2014-171529 A1 | 9/2014 |
| JP | 2017-011420 A1 | 1/2017 |
| JP | 2017-046096 A1 | 3/2017 |

OTHER PUBLICATIONS

Chinese Office Action (Application No. 201880073197.8) dated Feb. 1, 2021 (with English translation).

* cited by examiner

NURSE CALL SYSTEM

This application is a Continuation of International Application No. PCT/JP2018/015903 filed on Apr. 17, 2018, which claims the benefit of the Japanese Patent Application No. 2017-220234 filed on Nov. 15, 2017, No. 2018-034649 filed on Feb. 28, 2018, No. 2018-051336 filed on Mar. 19, 2018, the disclosures of which are incorporated by reference herein in their entireties.

BACKGROUND OF THE INVENTION

Field of the Invention

The present invention relates to a nurse call system, and in particular, relates to a nurse call system that enables a call for a nurse even from outside of a hospital room.

Description of Related Art

In a nurse call system, when a call is made using a nurse call slave device provided to an individual bed, a nurse call master device provided at a nurse station, or the like is notified of the call, thereby an answering nurse and the calling patient are allowed to speak with each other.

In one of such nurse call systems, nurse call slave devices are configured wirelessly so that, even when a patient moves to the outside of a hospital room, the patient can make a nurse call (calling) from that place, thus improving convenience for patients (see, for example, Japanese Laid-Open Patent Publication No. 2005-236437).

SUMMARY OF THE INVENTION

The nurse call system in Japanese Laid-Open Patent Publication No. 2005-236437 enables a call for a nurse by operating a nurse call slave device carried by a patient even when the patient moves to the outside of a hospital room. However, in order to configure nurse call slave devices wirelessly, it is necessary to configure not only the nurse call slave device but also plate slave devices and the like wirelessly. Further, in order to enable speech, each nurse call slave device to be carried needs to be provided with a speech function, or a corridor light or the like needs to be provided with a speech function, which requires great system change.

Meanwhile, a nurse carries a mobile phone for answering a call, and base stations for transmitting/receiving a signal to/from the mobile phone are provided at appropriate intervals in a hospital ward. Therefore, without having to configure nurse call slave devices wirelessly, it becomes possible to make a nurse call no matter where a patient is, if the patient can call a nurse using the base station.

An object of the present invention is to provide a nurse call system in attempt to improve convenience for hospitalized patients, and in particular, a nurse call system that enables a call for a nurse from anywhere in a hospital ward.

In order to achieve the above object, the invention according to a first aspect includes a nurse call slave device provided for each of beds in a hospital room, for a hospitalized patient to call a nurse, a nurse call master device provided at a nurse station, for answering a call from the nurse call slave device, a plate slave device which is provided near the bed in the hospital room and to which the nurse call slave device is connected, a controller configured to control speech and communication among devices, and a plurality of nurse mobile phones connected to the controller via a PBX having a mobile phone exchange connection function and a base station having a mobile phone wireless transmission/reception function. The nurse mobile phones are carried by nurses for answering a call from the nurse call slave device. A plurality of patient mobile phones carried by hospitalized patients are connected to the controller via the base station and the PBX as with the nurse mobile phones. A location information transmitter configured to wirelessly transmit a location signal is provided at an appropriate location in a hospital, and a location management server configured to manage location information about each patient mobile phone is provided. Each patient mobile phone includes a location information communication unit, which is configured to receive the location signal transmitted from the location information transmitter and transmit the location signal with an ID of the patient mobile phone added thereto. Each patient mobile phone has both a hospital room ID and a nurse call slave device ID registered therein for specifying the patient carrying the patient mobile phone. The patient mobile phone is capable of performing a nurse call to transmit a call signal with the hospital room ID and the nurse call slave device ID added thereto, through a predetermined operation. When a nurse call operation is executed on the patient mobile phone, the controller acquires location information about the patient mobile phone from the location management server, generates a call signal including the location information, and transmits the call signal to the nurse call master device and at least one of the nurse mobile phones.

With the above configuration, a nurse can be called with a mobile phone, and thus it is possible to make a nurse call even from outside of a hospital room. Further, information for recognizing the calling source is added to a call signal, and the location information of the calling source is also included therein. Therefore, the nurse who answers the call can recognize the calling source and the location thereof, and thus can easily respond the call. In this way, it becomes possible to make a nurse call even from outside of a hospital room without configuring the nurse call slave devices wirelessly.

In the invention according to a second aspect based on the first aspect, cameras are provided at appropriate locations in a hospital room and a common area in a hospital ward, the location management server includes a camera location storage unit configured to store the location of each camera, and a camera specifying unit configured to specify the camera that is nearest to the patient mobile phone, and when the nurse call operation is performed on the patient mobile phone, the controller acquires information about the camera that is nearest the patient mobile phone on which the nurse call operation is performed, from the location management server, and transmits a video taken by the camera, together with the call signal transmitted through the nurse call operation.

With the above configuration, in the case of making a nurse call from the patient mobile phone, a video taken by the nearest camera is transmitted to the calling destination. Therefore, a nurse answering the call can recognize the condition of the patient from the video, and thus can easily address the patient.

In the invention according to a third aspect based on the second aspect, the location management server includes a corridor light location storage unit configured to store a location of each of corridor lights, and a corridor light specifying unit configured to specify the corridor light that is nearest the patient mobile phone, and when the nurse call operation is performed on the patient mobile phone, the controller acquires information about the corridor light that is nearest the patient mobile phone on which the nurse call operation is performed, from the location management server, and transmits a call occurrence signal to the corridor light, to cause the corridor light to perform a nurse call occurrence notification operation.

With the above configuration, in the case of making a nurse call from the patient mobile phone, the nearest corridor light operates to perform notification of occurrence of the nurse call. Therefore, the nurse who comes in response to the call can easily recognize the patient who has made the nurse call, and thus can smoothly address the patient.

In the invention according to a fourth aspect based on the third aspect, the corridor light includes a corridor light monitor configured to display patient information as an image, the controller transmits the call occurrence signal with hospital room number information and bed number information added thereto, the hospital room number information and the bed number information being read from information about the hospital room ID and the nurse call slave device ID included in the call signal transmitted from the patient mobile phone, and the corridor light that has received the call occurrence signal displays the hospital room number information and the bed number information on the corridor light monitor.

With the above configuration, by looking at the corridor light that is performing notification of occurrence of the nurse call, the nurse can recognize who the patient is, and thus can execute a nursing work smoothly.

In the invention according to a fifth aspect based on any one of the first to fourth aspects, a shop terminal configured to manage an order from the hospitalized patient is provided at a shop in the hospital, and the patient mobile phone has a function of accessing the shop terminal and ordering a commodity, and through an ordering operation, the hospital room ID and the nurse call slave device ID are transmitted together with information about a commodity ordered from the patient mobile phone, to the shop terminal, so as to allow an ordering source to be recognized on the shop terminal.

With the above configuration, it is possible to order a commodity without going to a shop, and this is convenient for hospitalized patients. In addition, on the shop side, the ordering source patient can be recognized, and thus sales can be easily managed.

In the invention according to a sixth aspect based on any one of the first to fifth aspects, the patient mobile phone has a function of accessing an accounting server configured to manage an expense charged to each hospitalized patient in the hospital, so as to be capable of acquiring information about an expense charged to the patient associated with the patient mobile phone, from the accounting server.

With the above configuration, hospitalization expenses can be recognized on the patient mobile phone, whereby anxiety of the hospitalized patient about payment of hospitalization expenses can be mitigated.

In the invention according to a seventh aspect based on any one of the first to sixth aspects, the hospital room ID and the nurse call slave device ID registered on the patient mobile phone are registered by software for which a term of validity is set.

With the above configuration, since the function that enables calling for a nurse is terminated after a certain period has elapsed, possible confusion because of neglecting deletion can be avoided by a patient's owned mobile phone.

According to the present invention, a nurse can be called with a mobile phone, and a nurse call can be made even from outside of a hospital room. Further, information for recognizing the calling source and the location information of the calling source are included in a call signal. Therefore, the nurse who answers the call can recognize the calling source and the location thereof, and thus can easily respond the call. In this way, it becomes possible to make a nurse call even from outside of a hospital room without configuring the nurse call slave devices wirelessly.

DESCRIPTION OF THE PREFERRED EMBODIMENTS

Hereinafter, preferred embodiments of a nurse call system according to the disclosure will be described in detail with reference to the drawings.

Figure 1:
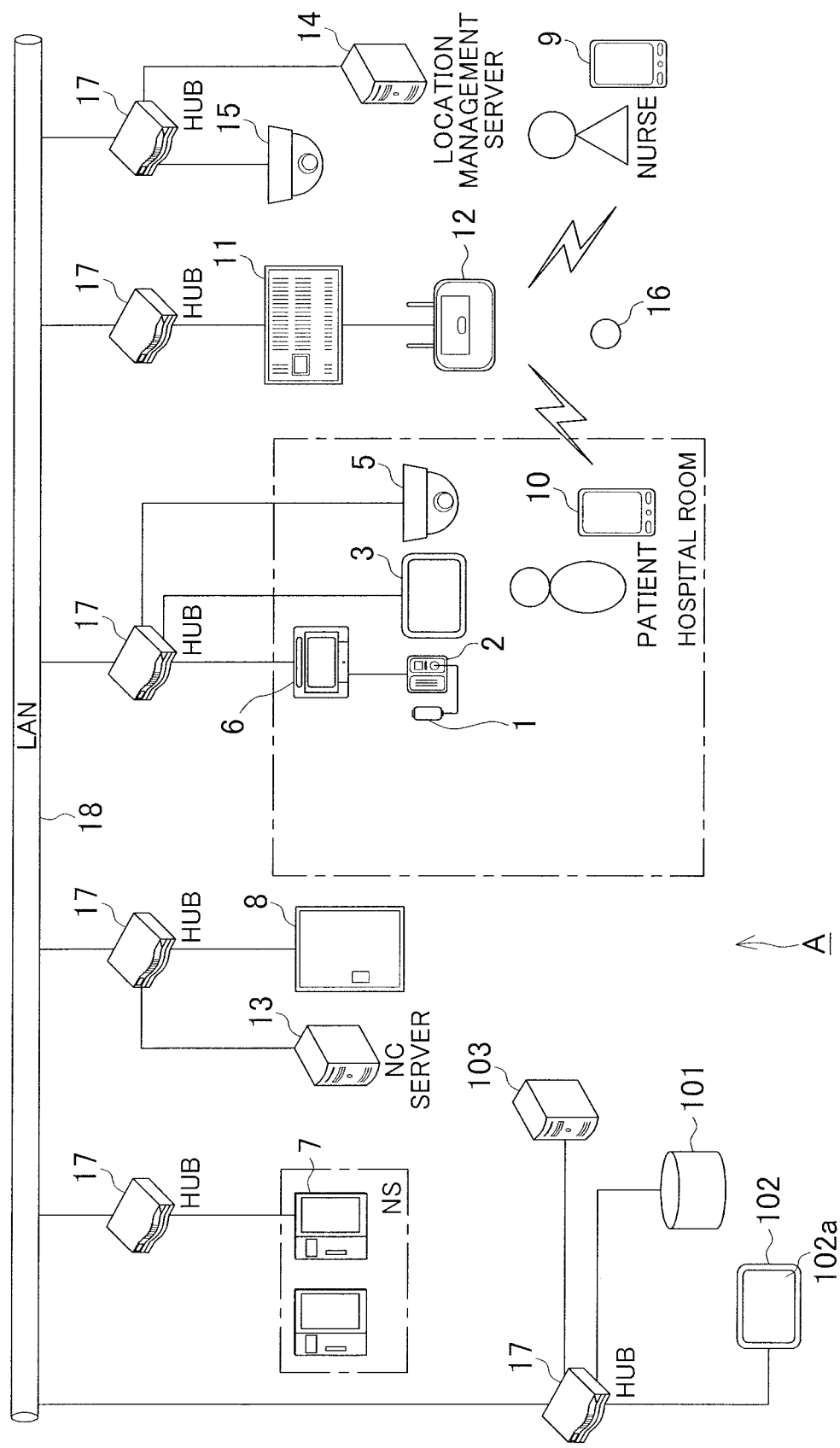
FIG. 1 shows the configuration of a nurse call system.

FIG. 1 is a configuration diagram of the nurse call system according to the present invention. As shown in FIG. 1, the nurse call system includes a nurse call slave device 1 provided for each bed in a hospital room for a hospitalized patient to call a nurse, a plate slave device 2 to which the nurse call slave device 1 is connected and which is provided to a wall surface near the bed in the hospital room, and a bedside monitor 3 provided for each bed in the hospital room and capable of displaying patient-related information. The nurse call system also includes a hospital room camera 5 capable of taking an image of a hospitalized patient on each bed in the hospital room, a corridor light 6 provided at a corridor wall surface near the hospital room, and a nurse call master device 7 provided in a nurse station for answering a call from the nurse call slave device 1. The nurse call system further includes a controller 8 configured to control devices such as the nurse call slave device 1, the corridor light 6, and the nurse call master device 7, a nurse mobile phone 9 carried by a nurse, and a patient mobile phone 10 carried by a hospitalized patient.

Further, the nurse call system includes an IP-PBX (hereinafter, simply referred to as "PBX") 11, which is connected to the controller 8 and has a mobile phone exchange connection function for managing communication between the nurse mobile phone 9 and the patient mobile phone 10. The nurse call system also includes a base station 12 having a mobile phone wireless transmission/reception function for performing wireless communication between the PBX 11 and the nurse mobile phone 9 or the patient mobile phone 10. The nurse call system further includes a nurse call server 13 storing various data about hospitalized patients, a location management server 14 configured to manage location information about the mobile phones, a common area camera 15 provided at a common area, and an indoor messaging system (IMES) transmitter 16.

The controller 8 of the nurse call system is communicable with an ordering system 101 which is another system and manages information in the hospital. The controller 8 of the nurse call system is also communicable with a shop terminal 102 which is provided in a shop and manages orders and sales of commodities, and an accounting server 103 for managing charged expenses such as treatment expenses for individual hospitalized patients.

Hereinafter, the nurse call system including the ordering system 101, the shop terminal 102, and the accounting server 103 is described as a nurse call system A.

The plate slave device 2 to which the nurse call slave device 1 is connected is connected to the corridor light 6 via a transmission line. The bedside monitor 3, the hospital room camera 5, the nurse call master device 7, the controller 8, the corridor light 6, the PBX 11, the nurse call server 13, the location management server 14, the common area camera 15, the ordering system 101, the shop terminal 102, and the accounting server 103 are connected to a LAN 18 provided in the hospital, via respective HUBs 17.

The PBX 11 is connected to the base station 12 via a transmission line. A plurality of base stations 12 are provided at appropriate locations in the hospital ward.

Figure 2:
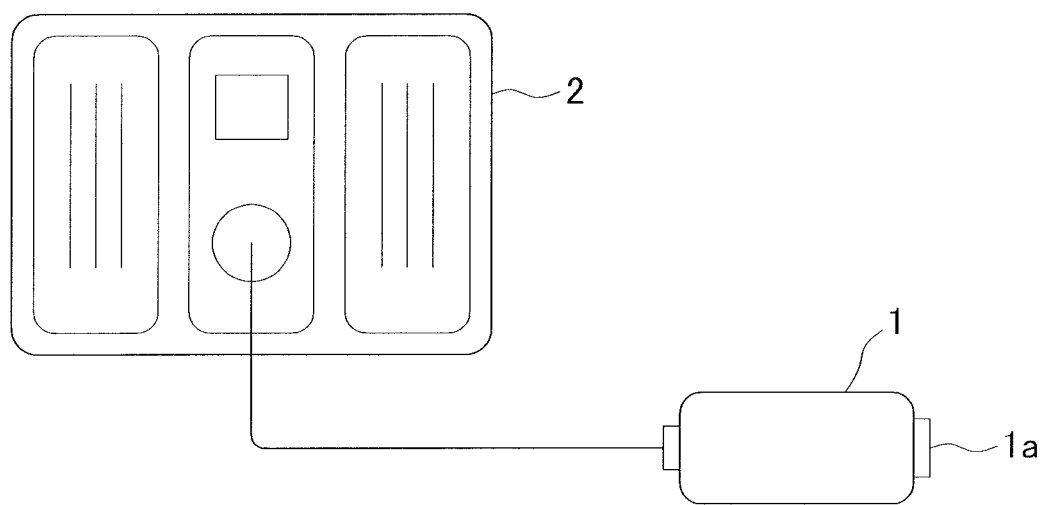
FIG. 2 shows a nurse call slave device and a plate slave device.

As shown in FIG. 2, the nurse call slave device 1 has a call button 1a for calling a nurse, and is connected to the plate slave device 2.

Figure 3:
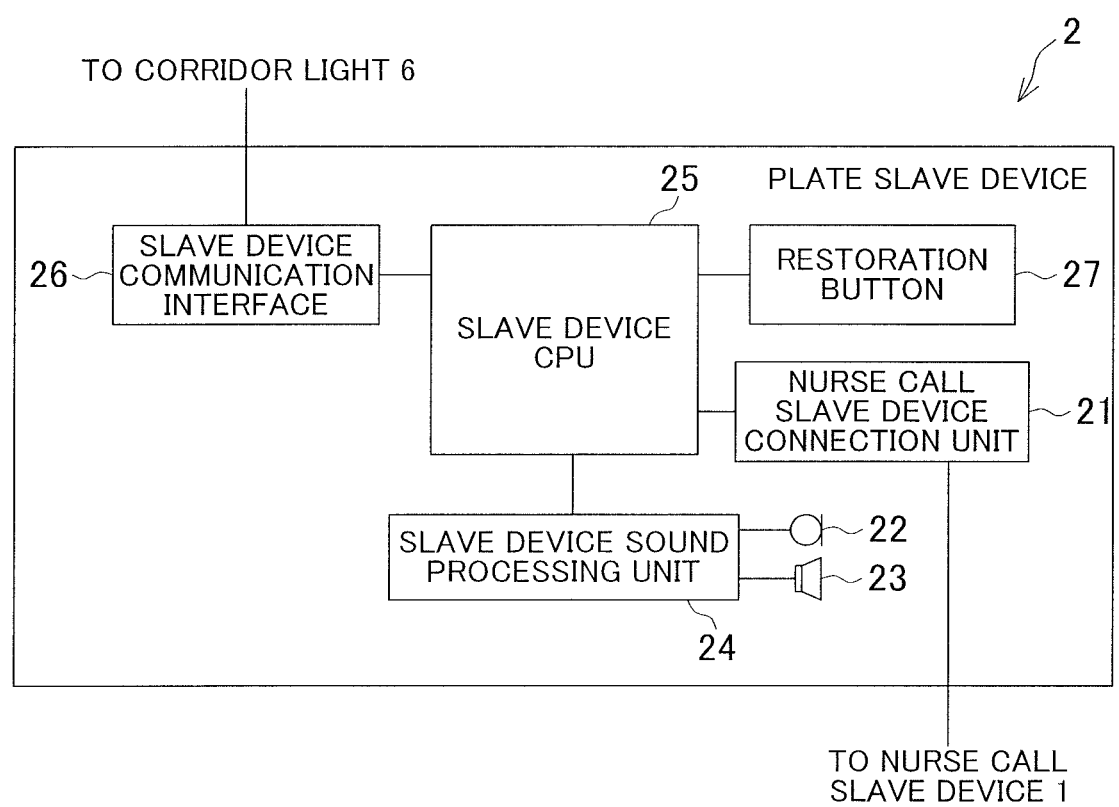
FIG. 3 is a function block diagram showing the configuration of the plate slave device.

As shown in FIG. 3, the plate slave device 2 includes a nurse call slave device connection unit 21 for making connection to the nurse call slave device 1, a microphone 22 and a loudspeaker 23 for speaking, a slave device sound processing unit 24 for processing a sound signal, a slave device CPU 25 for controlling the plate slave device 2, a slave device communication interface 26 for communicating with the corridor light 6, and a restoration button 27 for stopping a report operation and the like.

Figure 4:
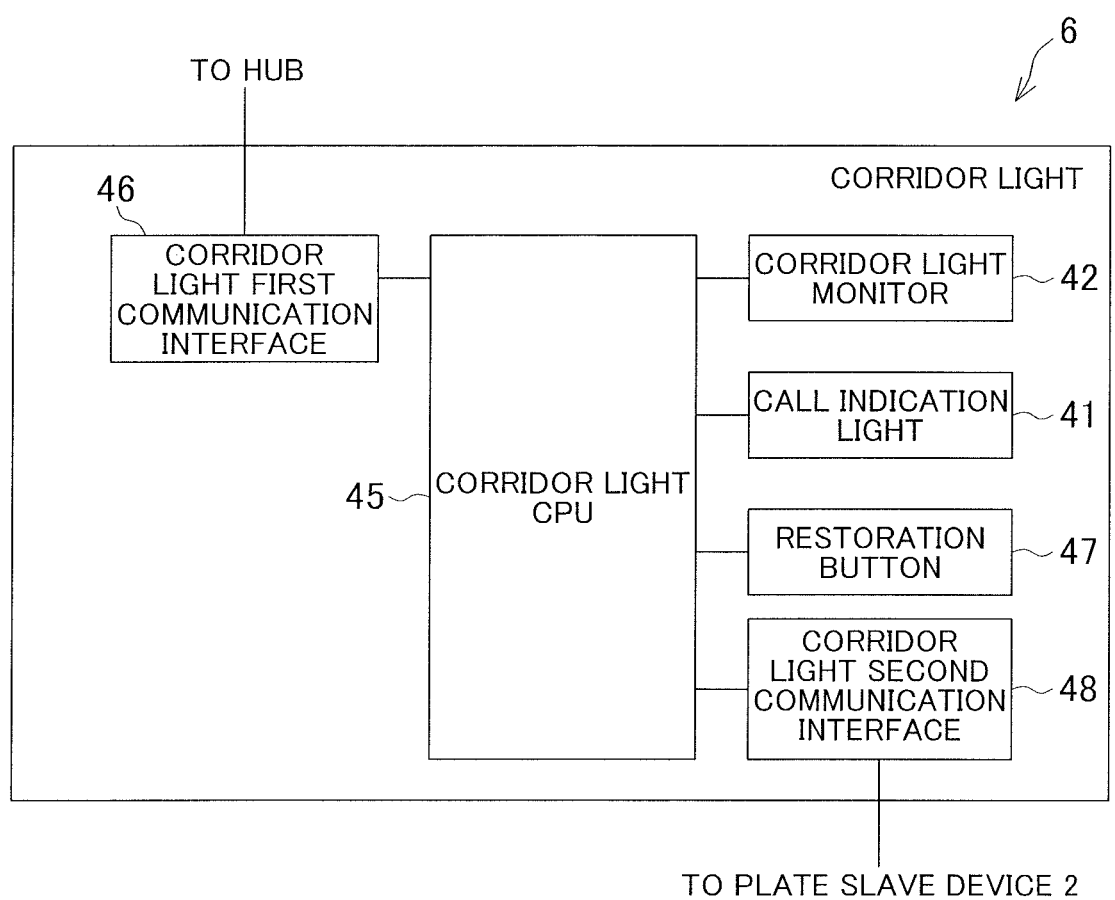
FIG. 4 is a function block diagram showing the configuration of a corridor light.

As shown in FIG. 4, the corridor light 6 includes a call indication light 41 for indicating occurrence of a call from a hospitalized patient by light emission, a corridor light monitor 42 formed of an LCD for displaying patient information such as the name of a patient in the hospital room, and a corridor light CPU 45 for controlling the corridor light 6. The corridor light 6 also includes a corridor light first communication interface 46 for communicating with the nurse call master device 7 and the like, a restoration button 47 for stopping a reporting operation, and a corridor light second communication interface 48 for communicating with the plate slave device 2.

Figure 5:
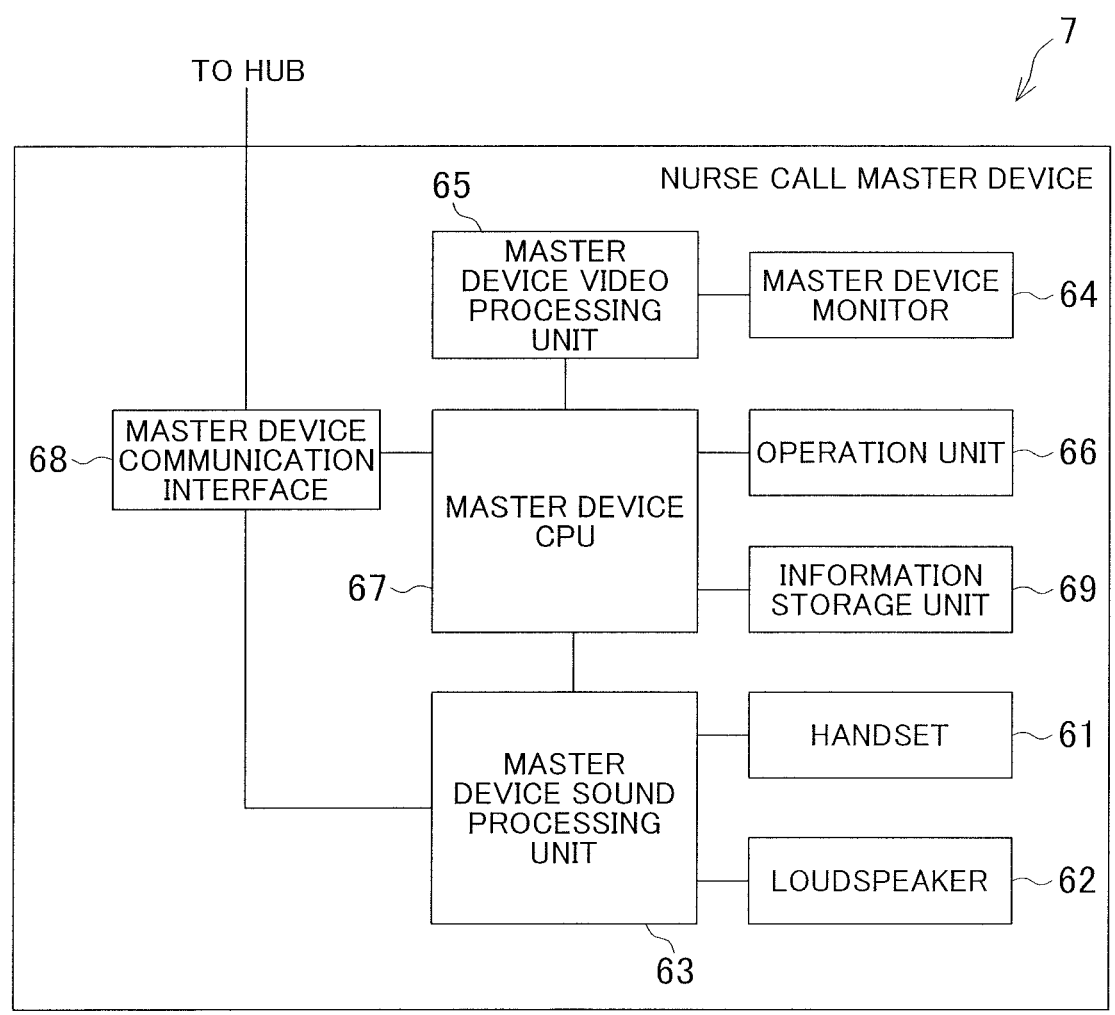
FIG. 5 is a function block diagram showing the configuration of a nurse call master device.

As shown in FIG. 5, the nurse call master device 7 includes a handset 61 for answering a call from the nurse call slave device 1, a loudspeaker 62 for emitting an alarm sound and the like, a master device sound processing unit 63 for processing a sound signal and processing an alarm sound, and a master device monitor 64 for displaying various information. The nurse call master device 7 also includes a master device video processing unit 65 for processing a video to be displayed on the master device monitor 64, an operation unit 66 formed of a touch panel for performing various operations, and a master device CPU 67 for controlling the entire nurse call master device 7. The nurse call master device 7 further includes a master device communication interface 68 for communicating with another device such as the controller 8, and an information storage unit 69 for storing various information.

Figure 6:
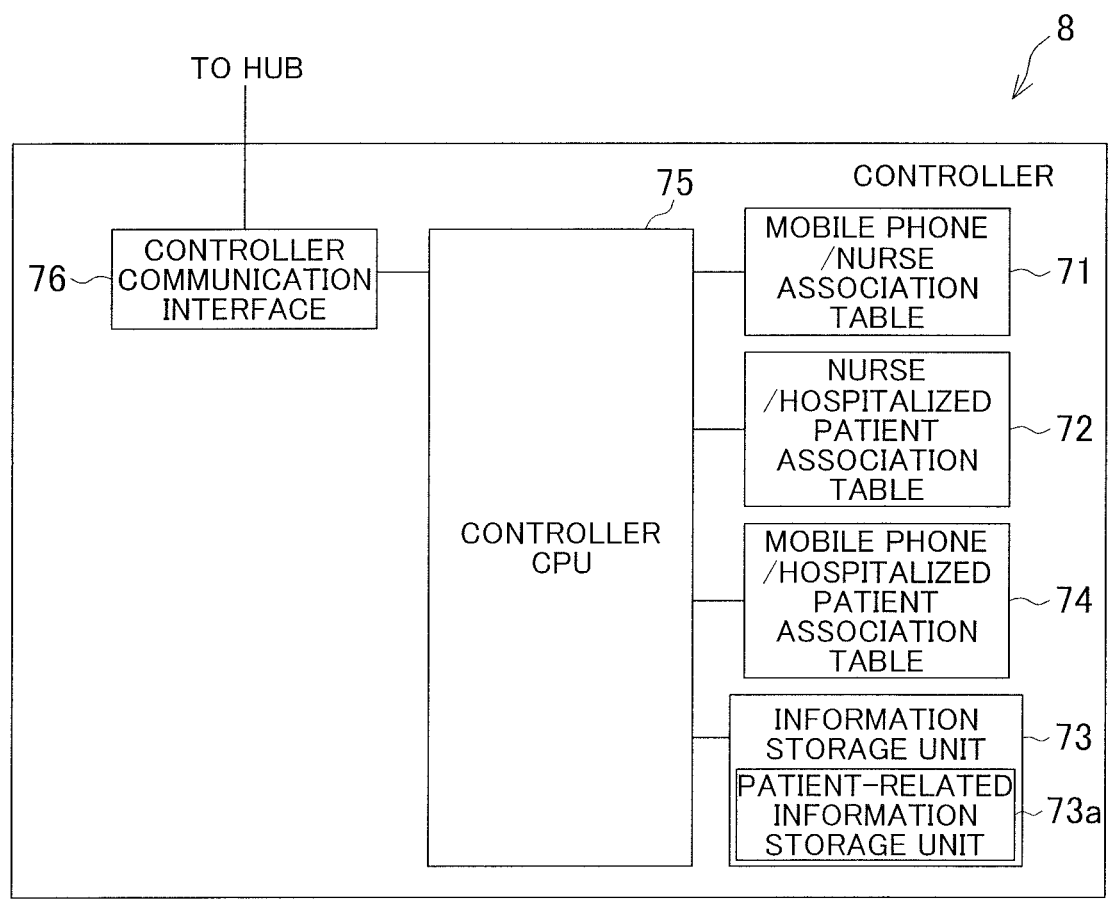
FIG. 6 is a function block diagram showing the configuration of a controller.

As shown in FIG. 6, the controller 8 includes a mobile phone/nurse association table 71 for storing the association between the nurse mobile phone 9 and each nurse, a nurse/hospitalized patient association table 72 for storing patients to which nurses are assigned, and an information storage unit 73. The controller 8 also includes a mobile phone/hospitalized patient association table 74 for storing the association between the patient mobile phone 10 and each hospitalized patient, a controller CPU 75 for controlling the controller 8, and a controller communication interface 76 for communicating with another device such as the corridor light 6.

The information storage unit 73 includes a patient-related information storage unit 73a for storing patient-related information. The patient-related information storage unit 73a stores patient information such as the name and age of a hospitalized patient, nursing information such as a nursing classification and a medical specialty of a hospitalized patient, the relationship between patient information and a hospital room ID and a slave device ID (nurse call slave device ID), phone number information of the patient mobile phone 10 carried by a patient, and the like. Such information is inputted through operation on the nurse call master device 7.

Each of the nurse mobile phone 9 and the patient mobile phone 10 is a multifunction terminal having a mobile phone function. These mobile phones, for example, a mobile phone called a smartphone can be used with predetermined application software installed thereon.

Thus, the nurse mobile phone 9 allows a nurse to answer a call from the nurse call slave device 1, and the patient mobile phone 10 allows a patient to call a nurse, i.e., make a nurse call as described later and, depending on setting, allows a patient to place an order to a shop and grasp the amount of payment to the hospital, for example.

The patient mobile phone 10 constitutes a location specifying system together with the IMES transmitter 16 and the location management server 14 described later. Therefore, the patient mobile phone 10 has, therein, a GPS communication unit (location information communication unit) (not shown) which specifies its own location by receiving satellite radio waves of a GPS and transmits the specified location information with its own ID added thereto.

Figure 7:
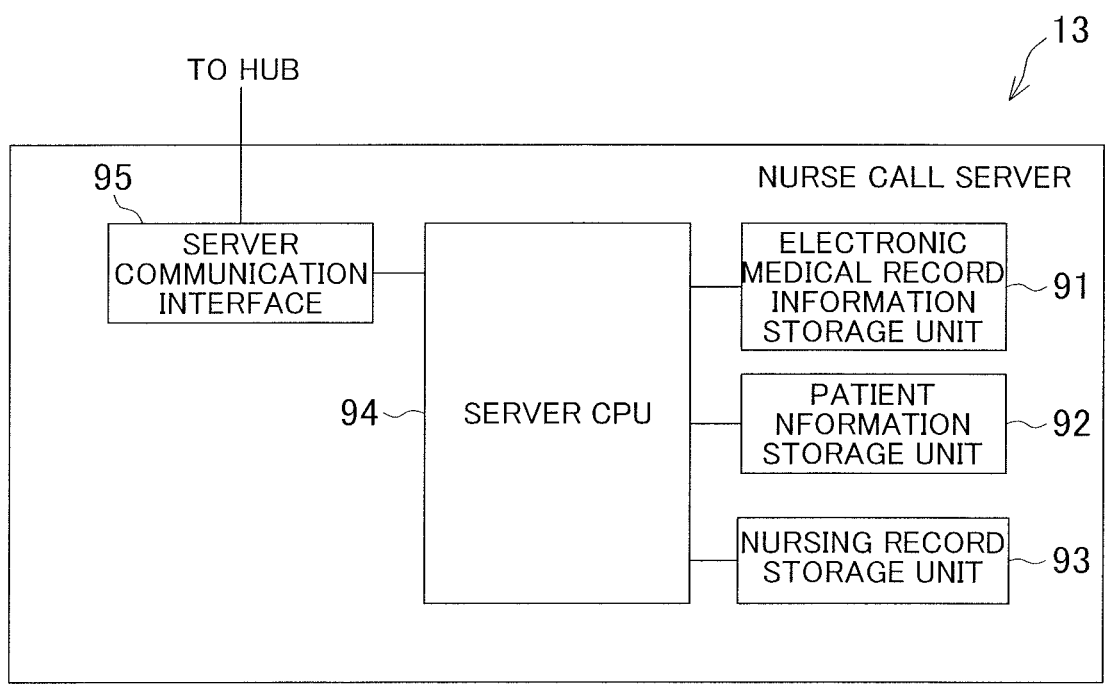
FIG. 7 is a function block diagram showing the configuration of a nurse call server.

As shown in FIG. 7, the nurse call server 13 includes an electronic medical record information storage unit 91 for storing a patient medical record inputted by a doctor, a patient information storage unit 92 for storing various patient information, a nursing record storage unit 93 for storing a nursing record inputted by a nurse, a server CPU 94 for controlling the nurse call server 13, and a server communication interface 95 for communicating with another device such as the controller 8.

Figure 8:
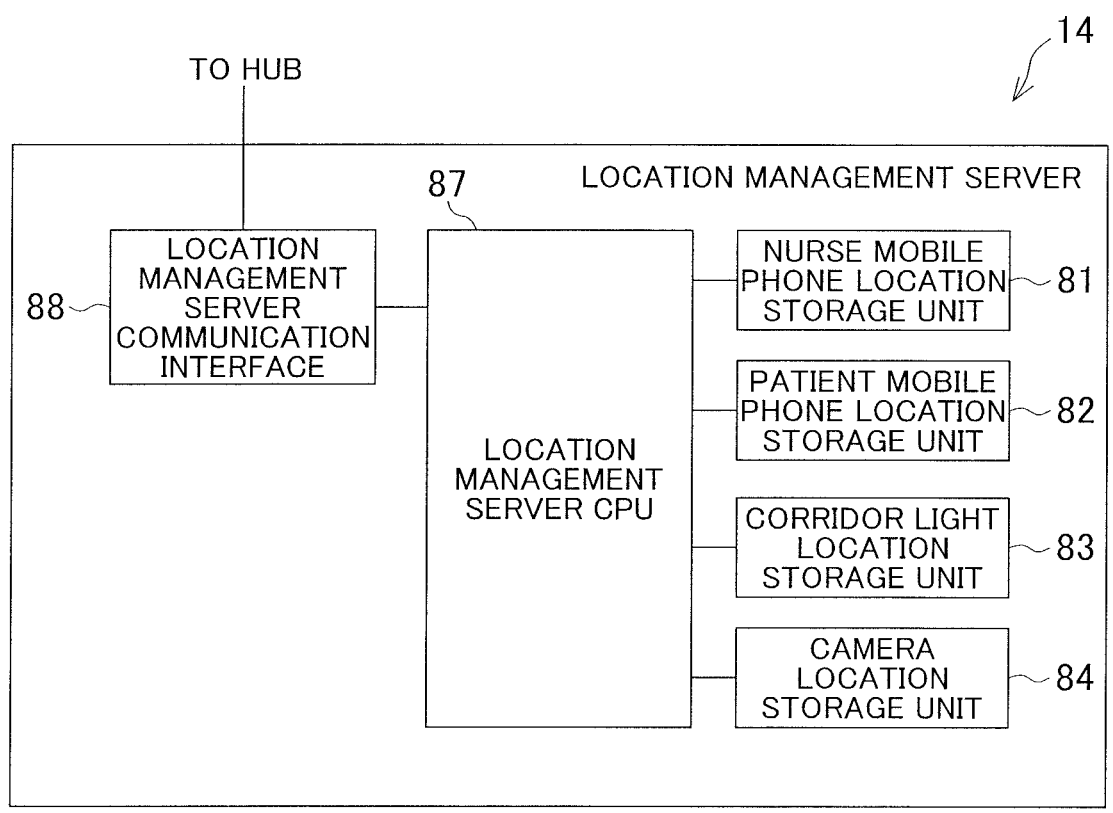
FIG. 8 is a function block diagram showing the configuration of a location management server.

As shown in FIG. 8, the location management server 14 includes a nurse mobile phone location storage unit 81 for storing the location of each nurse mobile phone, a patient mobile phone location storage unit 82 for storing the location of each patient mobile phone 10, a corridor light location storage unit 83 for storing the location of each corridor light 6, a camera location storage unit 84 for storing the locations of the hospital room camera 5 and the common area camera 15, a location management server CPU 87 which performs update control for the location information of the patient mobile phone 10, specifies the corridor light 6 that is nearest to the patient mobile phone 10, and controls the entire location management server 14, and a location management server communication interface 88 for communicating with another device such as the controller 8.

Each IMES transmitter 16 is a location information transmitter. The IMES transmitters 16 are provided at appropriate locations in the hospital ward or in the hospital, e.g., each hospital room, a nurse station, an operating room, a waiting room, a dayroom, a corridor, and the like, and constantly transmit own location information (location signals) by radio signals in the same radio wave format as the GPS radio waves.

The GPS communication unit provided in the patient mobile phone 10 receives location information transmitted from the near IMES transmitter 16 among the IMES transmitters 16, thereby recognizing its own location. Then, the GPS communication unit regularly transmits the recognized location information with an ID added thereto, to the location management server 14. The location information transmitted from the patient mobile phone 10 is received by the base station 12 as in the case of a normal speech signal, and then is transmitted via the PBX 11 and the LAN 18 to the location management server 14, so as to be stored therein. In this way, the location specifying system for recognizing the present location of each patient mobile phone 10 is established.

The common area cameras 15 are provided as appropriate in a common area in the hospital ward or in the hospital, e.g., common areas such as a corridor on each floor, a waiting room, and a dayroom. An image taken by each common area camera 15 can be displayed on the master device monitor 64 through operation on the operation unit 66 of the nurse call master device 7.

Operation of the nurse call system A configured as described above will be described below. Calling for a nurse from the nurse call slave device 1, call sound emitting operations of the nurse call master device 7 that has received the call and the nurse mobile phone 9 associated with the patient who is calling, and an answering operation on the nurse call master device 7 or the nurse mobile phone 9, are the same as in a conventional case. Therefore, the description of such operations is omitted, and here, a nurse call operation in which a patient calls a nurse using the patient mobile phone 10, and functions of placing an order to a shop and confirming a hospital expense, will be described.

As described above, location information of each patient mobile phone 10 is regularly transmitted to the location management server 14, and data in the patient mobile phone location storage unit 82 is rewritten and saved with the latest data through control by the location management server CPU 87.

On the patient mobile phone 10, predetermined application software is installed, and the hospital room ID and the slave device ID of the patient carrying this mobile phone are registered with use of this software.

First, a nurse call operation by the patient mobile phone 10 will be described. A nurse call is made with use of the nurse call slave device 1 in a hospital room, whereas, a nurse call is made by the patient mobile phone 10 carried by the patient outside a hospital room.

Figure 9:
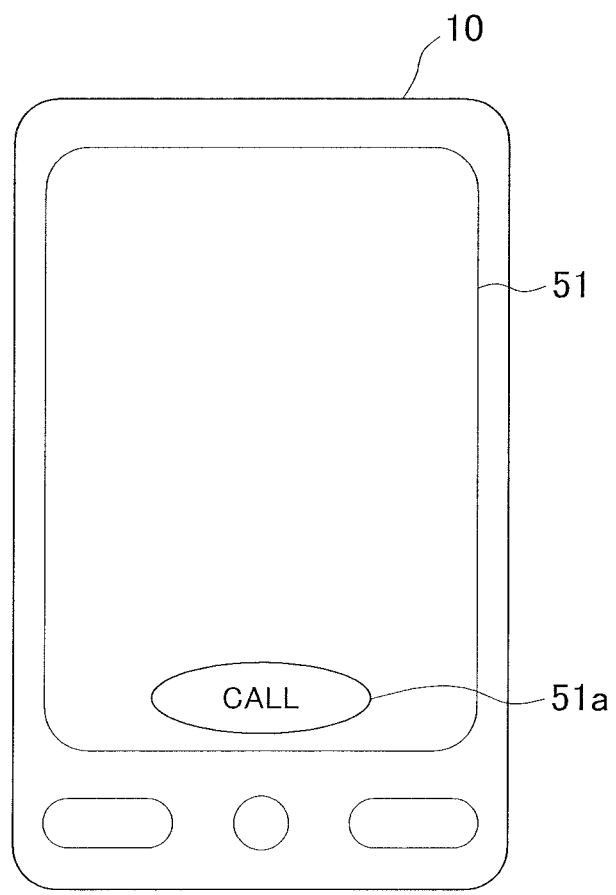
FIG. 9 shows a display screen of a patient mobile phone.

FIG. 9 illustrates the patient mobile phone 10. The patient mobile phone 10 has a display portion 51 provided with a touch panel. Through a predetermined operation by the patient, a call button 51*a* is displayed on the display portion 51 as shown in FIG. 9. When the call button 51*a* is touched, a call signal is transmitted to the controller 8 via the nearest base station 12 and the PBX 11. This call signal is similar to a call signal made by an operation on the nurse call slave device, and is transmitted with the hospital room ID and the slave device ID added thereto.

In the controller 8 that has received the call signal, first, the controller CPU 75 acquires the location information of the patient mobile phone 10 that is the transmission source of the call signal, from the location management server 14. In addition, from information about the hospital room ID and the slave device ID added to the call signal, the patient is specified by referring to the patient-related information storage unit 73*a*. The location information and the patient information acquired as described above are transmitted together with the call signal to the nurse mobile phone 9 carried by a nurse associated with the patient, by referring to the nurse/hospitalized patient association table 72 and the mobile phone/nurse association table 71.

The nurse mobile phone 9 that has received the call signal performs calling and at the same time, displays the transmitted patient information and location information, e.g., displays a text "Call from XX of Room YY, near Room ZZ". In addition, when the nurse call master device 7 has received the call signal, the patient information, and the location information, the nurse call master device 7 emits a call sound, performs blinking or the like of the patient information corresponding to the calling source in the displayed patient information list, and further displays the location information separately (not shown in detail).

Meanwhile, in the location management server 14, the location management server CPU 87 specifies the nearest corridor light 6 by referring to the corridor light location storage unit 83 on the basis of the location information of the patient mobile phone 10 on which the call operation has been performed, and notifies the controller 8 of the information about the specified corridor light 6. The controller 8 that has received this information executes indication control for the specified corridor light 6.

Specifically, in the controller 8 that has received the corridor light information, the controller CPU 75 transmits a call occurrence signal including the patient information of the calling source, to the specified corridor light 6. In the corridor light 6 that has received the call occurrence signal, through control by the corridor light CPU 45, the call indication light 41 performs indication operation, the patient information is read from the call occurrence signal, and the patient information is displayed on the corridor light monitor 42. As a result, for example, a text "Call from XX of Room YY" is displayed on the corridor light monitor 42.

Further, in the location management server 14, the location management server CPU 87 selects the common area camera 15 that is near the calling patient by referring to the camera location storage unit 84 on the basis of the location information of the patient mobile phone 10 on which the call operation has been performed, and notifies the controller 8 of information about the selected common area camera 15.

The controller 8 that has received the information about the selected common area camera 15 activates the specified common area camera 15 to transmit a taken video to the nurse call master device 7 and the nurse mobile phone 9 that is the calling destination.

On the nurse call master device 7 and the nurse mobile phone 9 to which the call signal has been transmitted as described above, call sounds are emitted, the patient information and the location information are displayed, and the video taken by the common area camera 15 is displayed.

As described above, a nurse can be called with use of a mobile phone (patient mobile phone 10), and thus a patient can make a nurse call even outside a hospital room. Further, information for recognizing the calling source is added to a call signal, and the location information of the calling source is also included therein. Therefore, the answering nurse can recognize the calling source as in the case of a call by the nurse call slave device 1, and thus can easily address the call. In this way, it becomes possible to call a nurse even from outside of a hospital room without configuring the nurse call slave devices 1 wirelessly. In addition, a patient can move away from the hospital room at ease.

In the case of making a nurse call from the patient mobile phone 10, a video taken by the nearest common area camera 15 is transmitted to the calling destination. Therefore, a nurse answering the call can recognize the condition of the patient from the video, and thus can easily address the patient.

Further, in the case of making a nurse call from the patient mobile phone 10, the nearest corridor light 6 operates to perform notification of occurrence of the nurse call. Therefore, the nurse who comes in response to the call can easily recognize the patient who has made the nurse call, and thus can smoothly address the patient. In addition, by looking at the corridor light 6 that is performing notification of occurrence of the nurse call, the nurse can recognize who the patient is, and thus can execute a nursing work smoothly.

Next, ordering of a commodity to a shop with use of the patient mobile phone 10 will be described. When software for accessing the shop terminal 102 is started through a predetermined operation on the patient mobile phone 10, an order screen appears and a list of orderable commodities acquired from the shop terminal 102 is displayed on the display portion 51. By performing a touch operation on a desired commodity on the display, an order signal for the touched commodity is transmitted via the controller 8 to the shop terminal 102, whereby the order is placed.

In the shop terminal 102 that has received the order signal, data of the commodity for which the order is placed is displayed on the display 102a, and the shop terminal 102 waits for processing by a shop clerk or the like. The order signal transmitted from the controller 8 to the shop terminal 102 at this time includes the patient information specified by the controller 8 on the basis of the hospital room ID and the slave device ID transmitted from the patient mobile phone 10, and thus information such as the hospital room number and the patient name of the ordering source is displayed together.

When the order process is performed by, for example, the clerk who has confirmed the display, an order completion signal is returned and completion of the order is indicated on the patient mobile phone 10. At the same time, the price (charged price) of the commodity is transmitted to the accounting server 103 and is accumulated together with the patient information of the ordering source.

It is noted that the commodity that has undergone the order process may be thereafter received by the patient at the shop, or may be delivered by the clerk to the patient who placed the order.

As described above, it is convenient for hospitalized patients since they can order a commodity without going to a shop. In addition, on the shop side, the ordering source patient can be recognized, and thus sales can be easily managed. Further, expense information such as the prices of purchased commodities is managed in the accounting server 103, thus enabling lump-sum payment at a later date.

In addition, by accessing the accounting server 103 in which expenses charged to patients, such as hospitalization expenses, are accumulated, an expense (charged expense) charged to each patient can be confirmed. By performing predetermined operation on the patient mobile phone 10 to start software for accessing the accounting server 103, and performing an expense confirmation operation, a confirmation signal with information about the hospital room ID and the slave device ID added thereto is transmitted to the accounting server 103 via the controller 8.

The accounting server 103 that has received the confirmation signal reads, from the accumulated data, charged expense data such as a hospitalization expense and the amount of payment to a shop associated with the requesting patient, and returns the read data to the patient mobile phone. As a result, list information about charged expenses such as the hospitalization expense associated with the patient is displayed on the patient mobile phone 10.

As described above, expense information such as a hospitalization expense can also be confirmed on the patient mobile phone 10, whereby anxiety of the hospitalized patient about the hospitalization expense can be mitigated.

As the application software that enables the patient mobile phone 10 to be used as the nurse call slave device 1, software using a one-time password with a term of validity is desirably used. In this case, since the function that enables calling for a nurse is terminated after a certain period has elapsed, possible confusion because of neglecting deletion can be avoided and a mobile phone owned by the patient can be used as the patient mobile phone 10.

When a call is made using the patient mobile phone 10 outside a hospital room, a video taken by the common area camera 15 is transmitted together with a call signal, whereas, when a nurse call is performed using the patient mobile phone 10 in a hospital room, the hospital room camera 5 is activated and a video taken by the hospital room camera 5 is transmitted.

Next, another nurse call system in an attempt to improve convenience for hospitalized patients will be described. Here, the corridor light 6 is provided with a call function, and the bedside monitor 3 is provided with a function for answering thereto. When a visitor who has arrived at a hospital room performs a call operation on the corridor light and there is no answer and the patient is absent, operation to report the location of the patient is performed. The nurse call system that performs this operation is described as a nurse call system B.

Figure 10:
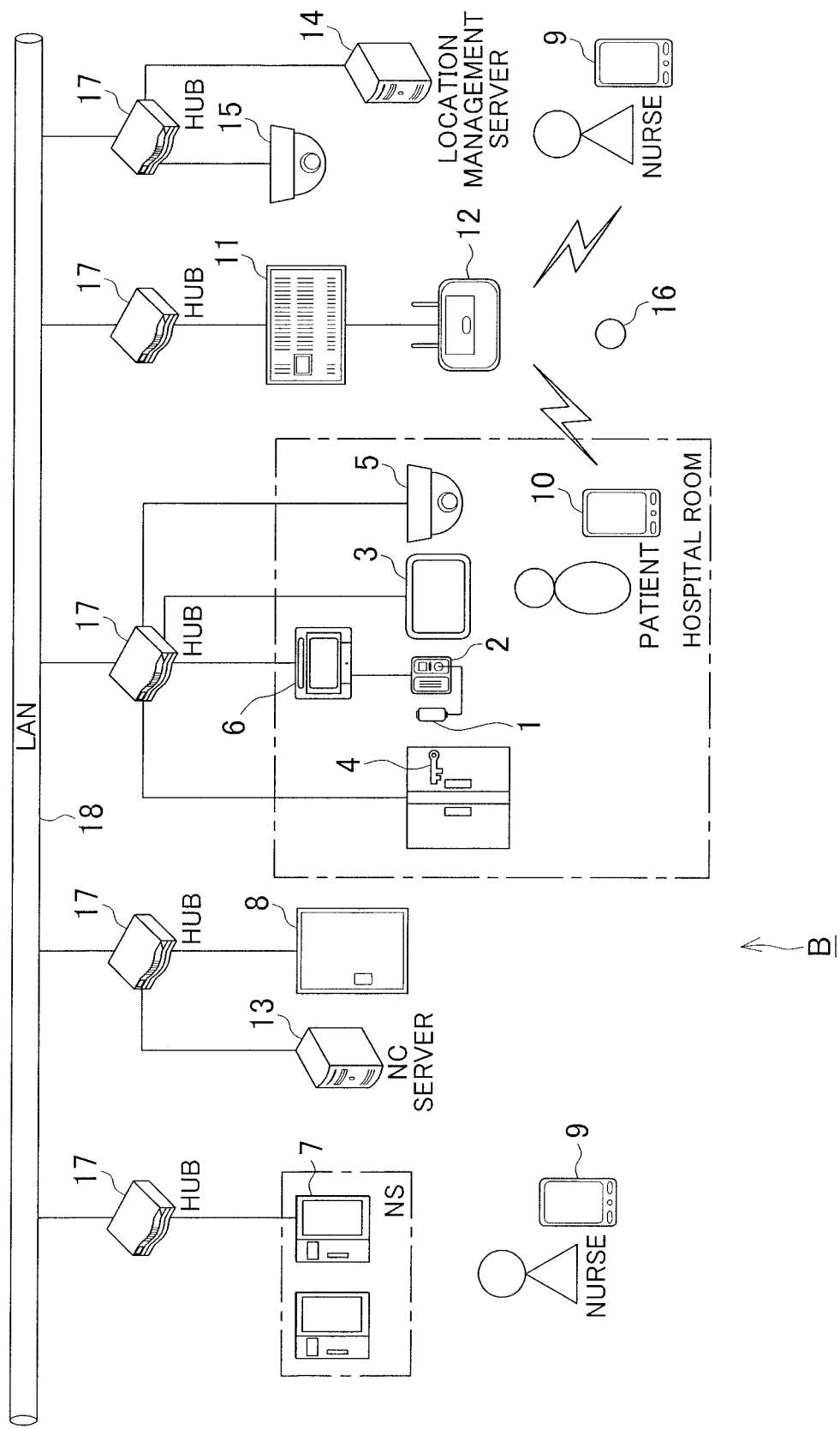
FIG. 10 shows another configuration of a nurse call system.

FIG. 10 shows the entire configuration of the nurse call system B. As in the configuration shown in FIG. 1 in the above embodiment, the nurse call system B includes the nurse call slave device 1, the plate slave device 2, the bedside monitor 3, the hospital room camera 5, the corridor light 6, the nurse call master device 7, the controller 8, the nurse mobile phone 9, the patient mobile phone 10, the PBX 11, the base station 12, the nurse call server 13, the location management server 14, the common area camera 15, and the IMES transmitter 16. Further, an electronic lock 4 provided to the door of the hospital room is connected to the LAN 18.

Figure 11:
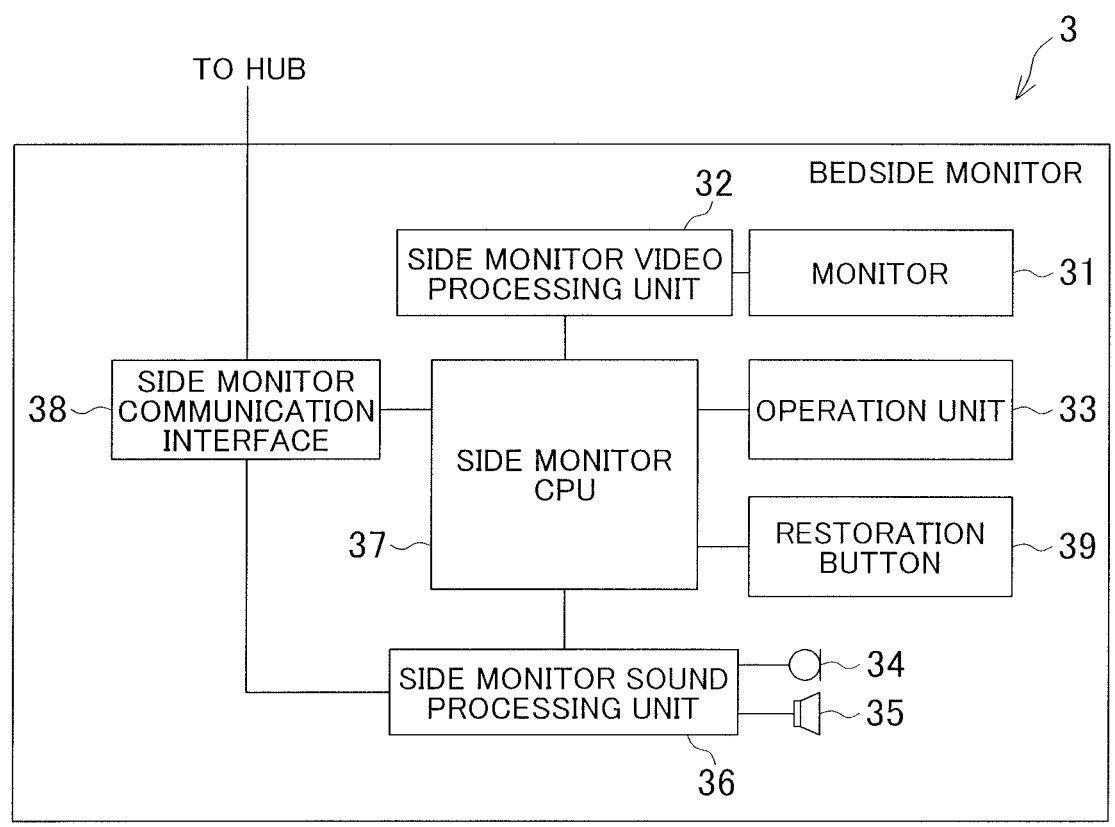
FIG. 11 is a function block diagram showing the configuration of a bedside monitor.

As shown in FIG. 11, the bedside monitor 3 of the nurse call system B includes a monitor 31 for displaying various information, a side monitor video processing unit 32 for processing a video to be displayed on the monitor 31, an operation unit 33 formed of a touch panel for performing various operations, a microphone 34 and a loudspeaker 35 for speaking, a side monitor sound processing unit 36 for processing a sound signal, a side monitor CPU 37 for controlling the bedside monitor 3, a side monitor communication interface 38 for communicating with the corridor light 6, and a restoration button 39 for performing operations such as stopping a report operation or the like and turning on/off the liquid crystal display.

Figure 12:
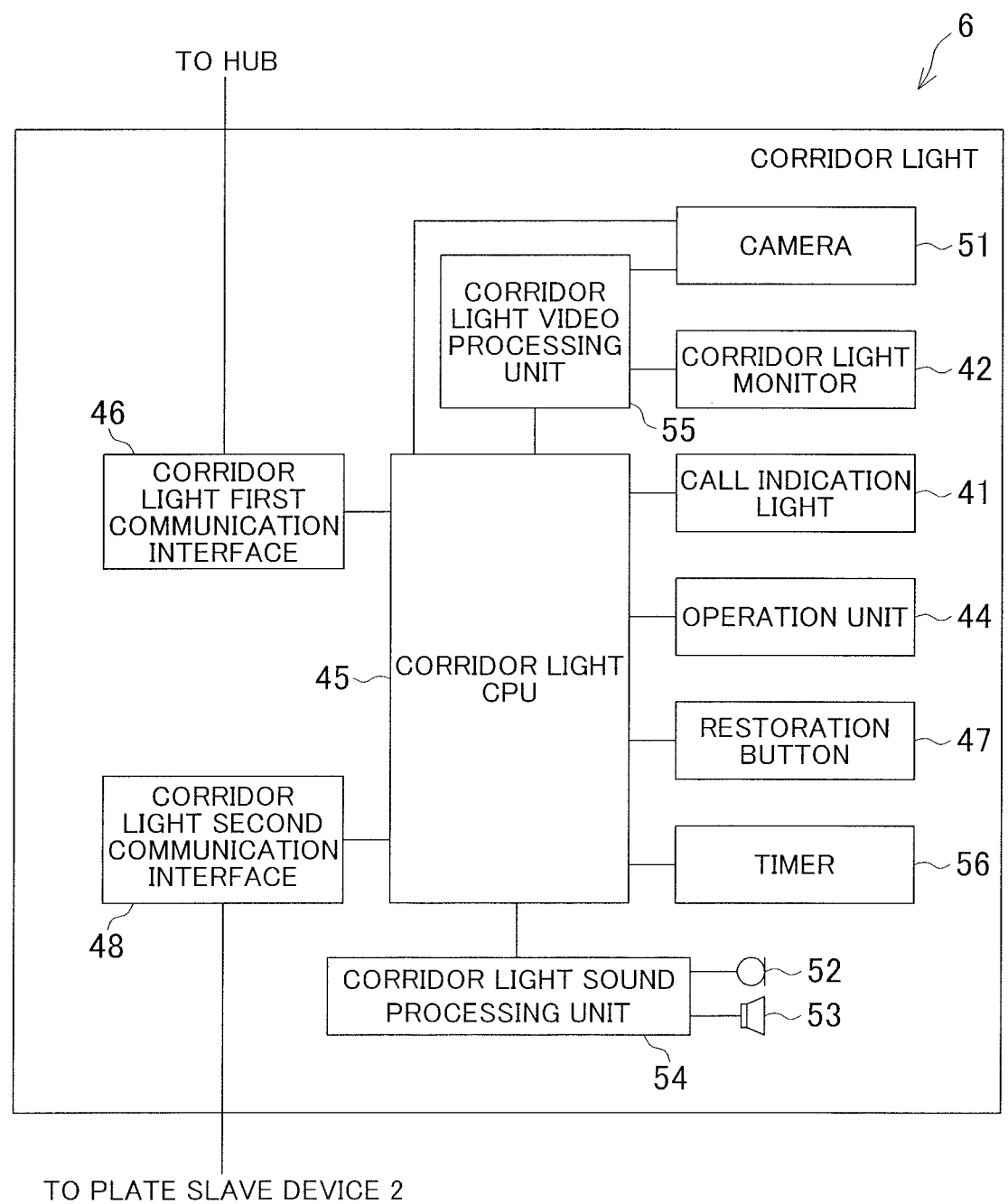
FIG. 12 is a function block diagram showing the configuration of a corridor light.

The corridor light 6 is configured as shown in FIG. 12. The corridor light 6 includes the call indication light 41, the corridor light monitor 42, the corridor light CPU 45, the corridor light first communication interface 46, the restoration button 47, and the corridor light second interface 48 shown above in FIG. 4, and further includes an operation unit 44 formed of a touch panel provided on the corridor light monitor 42, a camera 51 capable of taking an image of a visitor, a microphone 52 and a loudspeaker 53 for speaking, a corridor light sound processing unit 54 for processing a sound signal, a corridor light video processing unit 55 for processing a video to be displayed on the corridor light monitor 42, and a timer 56.

The patient-related information storage unit 73a of the controller 8 stores the nursing information about hospitalized patients and the relationship between the patient information, and the hospital room ID and the slave device ID (nurse call slave device ID) as described above, and further stores schedule information about examinations, surgeries, and the like of hospitalized patients, mobile phone information about the patient mobile phone 10 owned by each patient, meeting possible/impossible information indicating whether or not it is possible to meet a hospitalized patient, operation possible/impossible information indicating whether or not each hospitalized patient can perform a room entry permission operation, and the like. Such information is inputted through operation on the nurse call master device 7.

Figure 13:
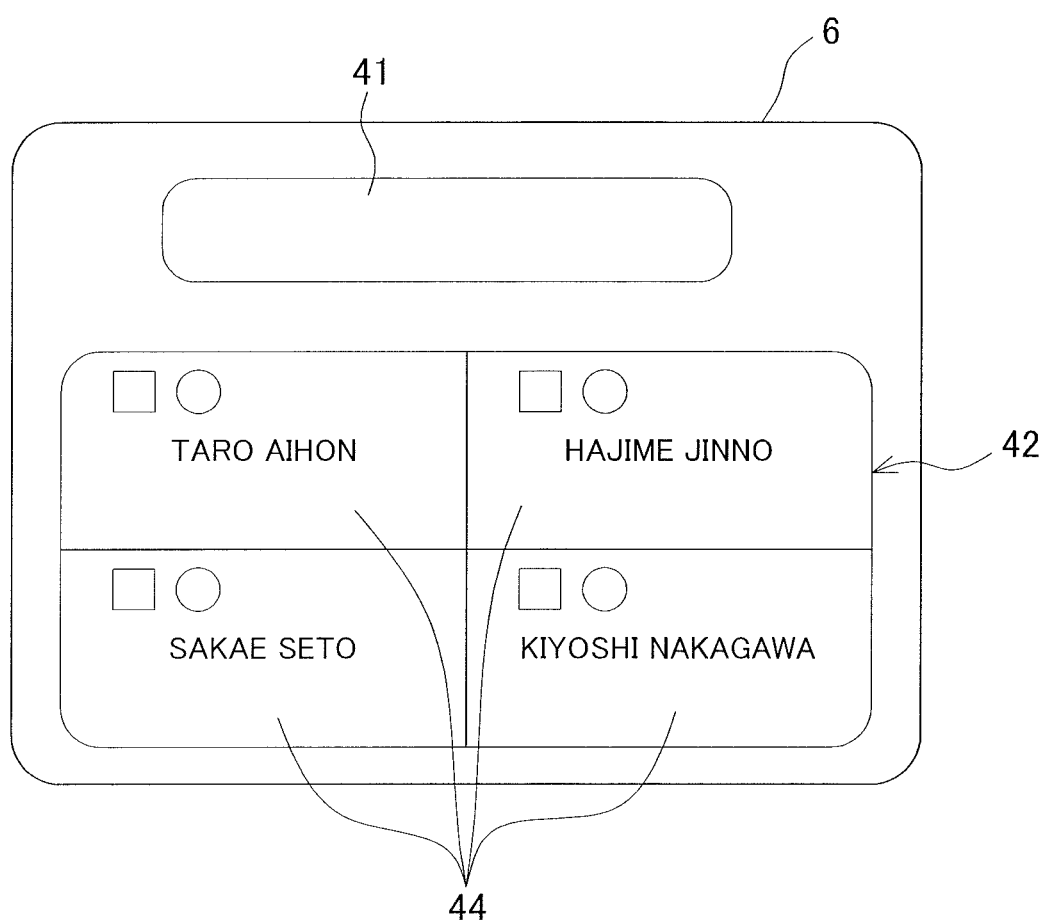
FIG. 13 shows an example of a display screen in a standby state of a corridor light monitor.

In a standby state when an operation by a visitor, or the like is not performed, the corridor light 6 displays the names of hospitalized patients hospitalized in the hospital room, on the corridor light monitor 42 as shown in FIG. 13, on the basis of information in the patient-related information storage unit 73a described later.

Figure 14:
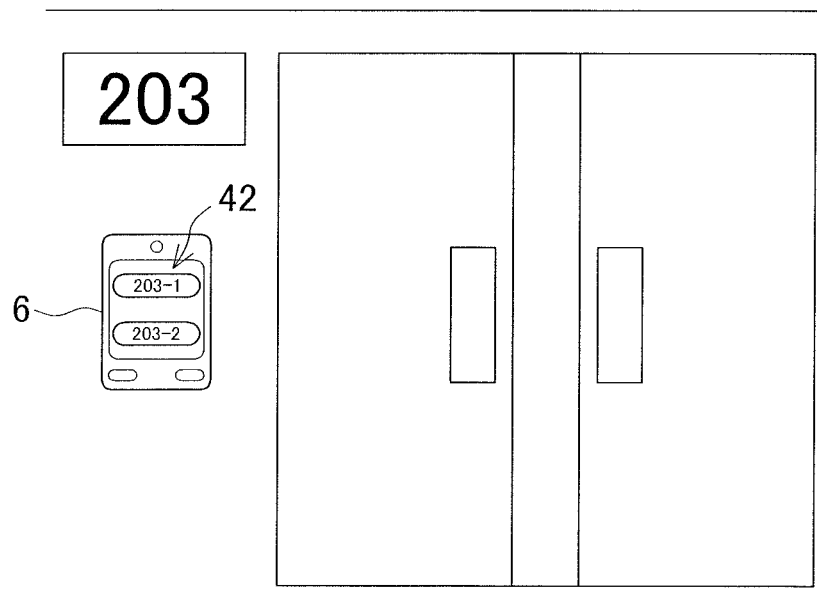
FIG. 14 shows another example of a display screen in a standby state of the corridor light monitor.

Regarding the display in the standby state, information such as the sexes and ages may be displayed together with the names of hospitalized patients, or as shown in FIG. 14, only the bed numbers in the hospital room may be displayed without displaying the names of hospitalized patients. The area in which the names and/or the bed numbers of hospitalized patients are displayed is formed as a touch panel, and thus forms the operation unit 44 in the present embodiment.

The patient mobile phone 10 can be used as the nurse call slave device as described above, and in addition, depending on setting, is capable of receiving a call signal from a visitor and answering thereto.

Figure 15:
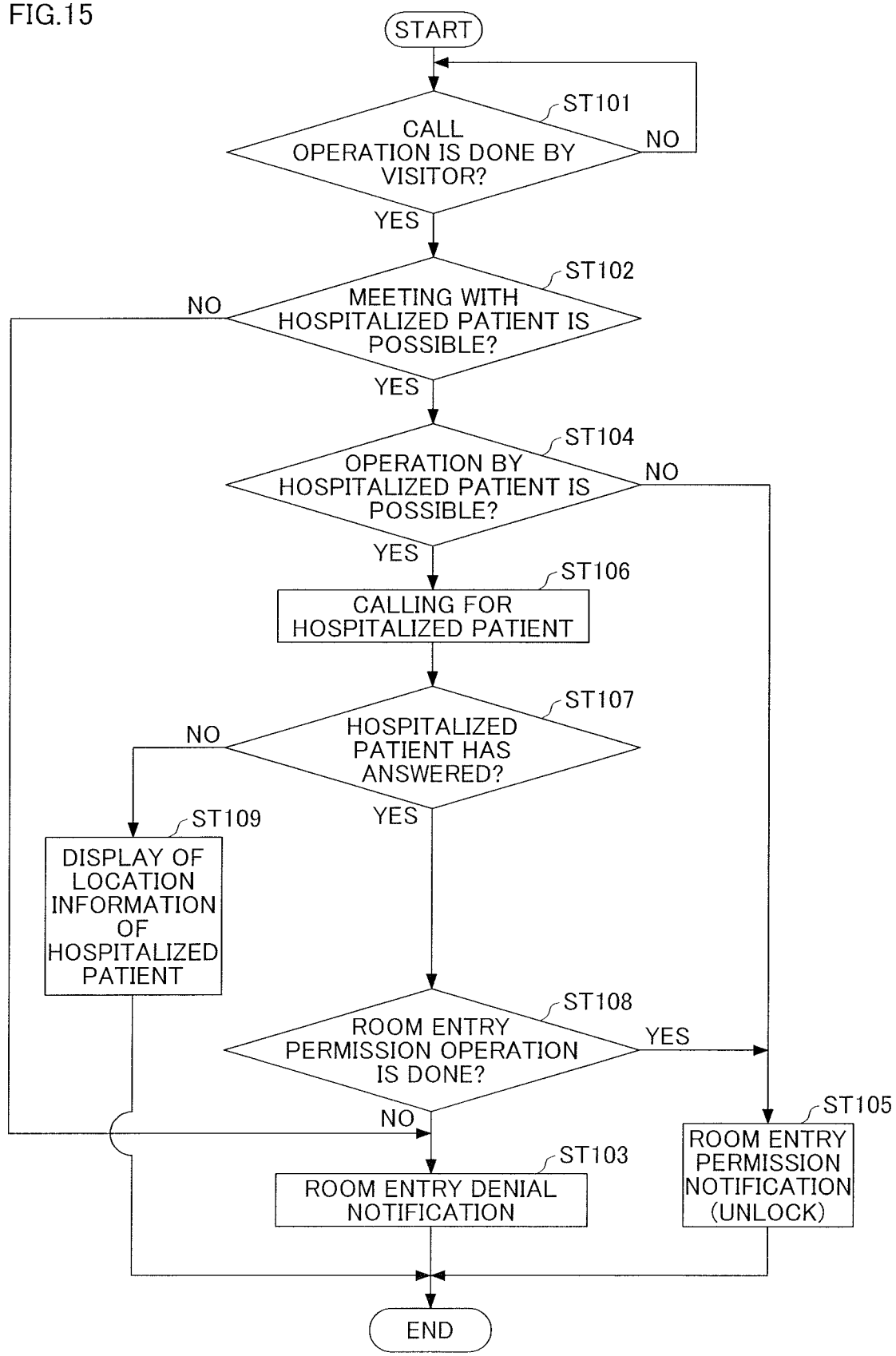
FIG. 15 is a flowchart showing operation of the nurse call system.

Operation of the nurse call system B configured as described above, in particular, operation in the case where a visitor performs a call operation on the corridor light 6 will be described below, with reference to FIG. 15. Here, setting is made such that a call signal from a visitor is to be transmitted to the bedside monitor 3.

In a standby state, the names of hospitalized patients hospitalized in the hospital room are displayed on the corridor light monitor 42 of the corridor light 6, as shown in FIG. 13.

A visitor touches an area (operation unit 44) on which the name of a hospitalized patient is displayed, to call the hospitalized patient.

To describe further, when an area on which the name of a hospitalized patient is displayed is touched by a visitor, the corridor light CPU 45 determines that a call button has been operated (ST101: Yes) and then the corridor light CPU 45 starts imaging by the camera 51. In addition, first, reads meeting possible/impossible information about the called hospitalized patient from the patient-related information storage unit 73a, to determine whether it is possible to meet the hospitalized patient (ST102).

If the corridor light CPU 45 determines that it is not possible to meet the hospitalized patient or a meeting impossible setting is made (ST102: No), the corridor light 6 reports that room entry is denied (ST103). Specifically, a message "Meeting is not allowed now" is displayed on the corridor light monitor 42. In this case, the corridor light CPU 45 does not notify the bedside monitor 3 that the call is made.

In the present embodiment, the report that room entry is denied is performed by displaying a message on the corridor light monitor 42. However, without limitation thereto, for example, the loudspeaker 53 may report by sound that meeting is not allowed, in addition to display of a message, or a report may be performed by sound only.

If the corridor light CPU 45 determines that it is possible to meet the hospitalized patient (ST102: Yes), the corridor light CPU 45 reads the operation possible/impossible information for the called hospitalized patient from the patient-related information storage unit 73a, to determine whether or not the hospitalized patient can perform an operation for permitting room entry (ST104).

When the corridor light CPU 45 determines that the hospitalized patient cannot perform an operation for permitting room entry (ST104: No), the corridor light CPU 45 unlocks the electronic lock 4 (ST105).

On the other hand, if the corridor light CPU 45 determines that the hospitalized patient can perform an operation for permitting room entry (ST104: Yes), the corridor light CPU 45 starts the timer 56, transmits a call signal to the bedside monitor 3 associated with the name touched by the visitor, and transmits image data taken by the camera 51 thereto.

When the side monitor CPU 37 of the bedside monitor 3 has received the call signal from the corridor light CPU 45, the side monitor CPU 37 emits a call sound from the loudspeaker 35, and displays the image data of the camera 51 transmitted from the corridor light CPU 45, on the monitor 31 (ST106). Through this operation, the patient who is visited is notified that the visitor has come. The hospitalized patient who is called as described above can establish a speech condition with the corridor light 6 or can perform an operation of permitting or not permitting room entry, by operating the operation unit 33 within a predetermined time period set on the timer 56 in advance.

That is, in the side monitor CPU 37, if an answering operation is performed within the predetermined time period set on the timer 56 in advance through an operation on the operation unit 33 by the hospitalized patient (ST107: Yes), the corridor light CPU 45 controls the microphone 34 and the loudspeaker 35 of the bedside monitor 3 and the microphone 52 and the loudspeaker 53 of the corridor light 6 so as to establish a speech condition between the bedside monitor 3 and the corridor light 6. Thus, the hospitalized patient can speak with the visitor. This speech channel establishment is performed through control by the corridor light CPU 45. However, this speech channel establishment may be performed through control by the side monitor CPU 37.

Then, when the hospitalized patient has performed an operation of permitting room entry by operating the operation unit 33 (ST108: Yes), the side monitor CPU 37 transmits a room entry permission notification signal to the corridor light 6. When the corridor light CPU 45 has received the room entry permission notification signal, the corridor light CPU 45 unlocks the electronic lock 4.

On the other hand, when the hospitalized patient has performed an operation of not permitting room entry by operating the operation unit 33 (ST108: No), the side monitor CPU 37 transmits a room entry non-permission notification signal to the corridor light 6. When the corridor light CPU 45 has received the room entry non-permission notification signal, the corridor light CPU 45 displays a message "meeting is not allowed now" on the corridor light monitor 42 (ST103). As previously described, the manner of a report that room entry is denied is not limited thereto.

If such an operation on the operation unit 33 by the hospitalized patient is not performed within the predetermined time period set on the timer 56 (ST107: No), the corridor light CPU 45 reads the schedule information about the called hospitalized patient from the patient-related information storage unit 73a. Then, if there is a schedule at that time, the corridor light CPU 45 reports the corresponding location. Specifically, the corridor light CPU 45 displays the text "the patient is in the consultation room now" or the like on the corridor light monitor 42 (ST109), indicating the location based on the schedule In the present embodiment, a report of the location of the hospitalized patient is performed through a message displayed on the corridor light monitor 42. However, without limitation thereto, for example, the location may be reported by sound from the loudspeaker 53, in addition to display of a message, or the location may be reported by sound only.

As described above, in the nurse call system B according to the present embodiment, since the location based on the schedule of the hospitalized patient can be reported to the visitor when the called hospitalized patient is not in the hospital room, the visitor can meet the hospitalized patient by going to the reported location.

In addition, since the called hospitalized patient can operate the operation unit 33 to perform an operation of permitting room entry, the hospitalized patient can determine permission/non-permission of the room entry for each visitor.

Further, when meeting is difficult as in a state in which no visitors are allowed or a patient does not feel like meeting visitors, the meeting possible/impossible information stored in the controller 8 can be set into a meeting impossible state. Since notification that room entry is denied can be performed to the visitor even when the hospitalized patient is in the hospital room, burden on a hospitalized patient for responding to visitors can be reduced. In addition, if a meeting impossible setting is made, the hospitalized patient is not called when a visitor has made a call. Therefore, the hospitalized patient is not bothered by a call sound or the like when a call is made, so that burden on the hospitalized patient can be reduced. Further, in this case, even when the hospitalized patient is not in the hospital room, the location information is not reported to the visitor, thus making a meeting impossible setting leads to privacy improvement.

In the nurse call system B according to the present embodiment, registration of schedule information or setting of meeting possible/impossible information to the patient-related information storage unit 73a of the controller 8 is performed from the nurse call master device 7. However, addition of schedule information or meeting impossible setting may be allowed to be made from the bedside monitor 3 or the like. Thus, the hospitalized patient can register schedule information in more detail. In addition, the hospitalized patient can easily make a meeting impossible setting when the hospitalized patient does not feel like meeting visitors.

Alternatively, only nurses, instead of hospitalized patients, may be allowed to make registration of schedule information or setting of meeting possible/impossible information from the bedside monitor 3.

In the nurse call system B according to the present embodiment, since the electronic lock 4 is mounted to the door of the hospital room, the hospitalized patient can avoid meeting the visitor who the patient doesn't want to meet if the hospitalized patient determines not to perform an unlocking operation. Thus, hospitalized patients can stay in the hospital at ease. In addition, when room entry is permitted, the electronic lock can be automatically unlocked, whereby physical burden on the hospitalized patient for moving to the door can be eliminated.

In the present embodiment, the electronic lock 4 is mounted to the door of the hospital room as described. If such an electronic lock is not provided to the door of the hospital room, the corridor light CPU 45 displays a message for permitting room entry, e.g., "Please come in", on the corridor light monitor 42, when a room entry permission notification signal is received. The report that meeting is allowed may be performed by sound from the loudspeaker 53, in addition to display of such a message, or the report may be performed by sound only.

In the nurse call system B according to the present embodiment, the call device of the present invention is formed by the corridor light 6 which is provided in front of a hospital room for reporting a call from the nurse call slave device 1 to a nurse and which has the corridor light monitor 42 for displaying the corresponding patient information in the hospital room. Thus, utilizing a known corridor light enables the configuration at a low cost.

In the present embodiment, the case where the call device of the present invention is formed by the corridor light 6 has been described. However, any device may be adopted as long as the device is provided in front of a hospital room and allows a visitor to call a hospitalized patient in the hospital room before entering the room. For example, a device like an intercom at an entrance may be adopted.

The bedside monitor 3 and the corridor light 6 in the nurse call system B according to the present embodiment each have a microphone and a loudspeaker, and when the side monitor CPU 37 has received a call signal from the corridor light 6, a speech condition is established through operation on the operation unit 33. Therefore, the called hospitalized patient can speak with the visitor, and thus can confirm who the visitor is and the purpose of the visit, before room entry operation.

In the nurse call system B according to the present embodiment, when the side monitor CPU 37 of the bedside monitor 3 has received a call signal from the corridor light CPU 45, image data of the camera 51 transmitted from the corridor light CPU 45 is displayed on the monitor 31.

Therefore, the called hospitalized patient can confirm the face of the visitor through the bedside monitor, and thus can easily confirm who the visitor is, before room entry operation.

In the above nurse call system B according to the present embodiment, the bedside monitor 3 is notified that a call is made, and an answering operation to the call notification is performed through operation on the operation unit 33 of the bedside monitor 3. However, without limitation thereto, at least one of the nurse call slave device 1, the plate slave device 2, the bedside monitor 3, and the patient mobile phone 10 may be notified of the call. In addition, an answering operation may be allowed to be performed on at least one of these.

In the case of adopting a configuration in which a call signal is transmitted to the nurse call slave device 1, it is necessary to provide a notification control unit for executing control for giving a notification that a call is made to the nurse call slave device 1, and in the case of adopting a configuration in which an answering operation is performed by the nurse call slave device 1, it is necessary to provide an operation unit thereto. In addition, in the case of adopting a configuration in which a call signal is transmitted to the patient mobile phone 10, the corridor light CPU 45 reads mobile phone information about the called hospitalized patient from the patient-related information storage unit 73*a*, and gives a notification of the call to the patient mobile phone of the hospitalized patient.

In the nurse call system B according to the present embodiment, the case where the controller 8 has the patient-related information storage unit 73*a* has been described. However, the nurse call master device 7 may have the patient-related information storage unit 73*a*, or another storage device may have the patient-related information storage unit 73*a*.

The corridor light 6 may further include a storage unit for storing image data taken by the camera 51. With this configuration, a record of visitors can be kept, and thus theft in the hospital room can be deterred.

<Modifications>

In the nurse call system B according to the above embodiment, if an operation on the operation unit 33 by a hospitalized patient is not performed within a predetermined time period set on the timer 56, the location based on the schedule information about the called hospitalized patient is reported. However, the present location of the hospitalized patient may be reported with use of the location specifying system of the patient mobile phone 10 described above.

In the nurse call system using the location specifying system, if an operation on the operation unit 33 by a hospitalized patient is not performed within a predetermined time period set on the timer 56, the corridor light CPU 45 refers to the mobile phone/hospitalized patient association table 74 of the controller 8 and the location management server 14 and reads location information about the patient mobile phone 10 of the called patient from the location management server 14, and then reports the location.

The other operations are the same as in the above embodiment of the nurse call system B.

Also in the nurse call system configured as described above, when a called hospitalized patient is not in the hospital room, the location based on the present location information about the hospitalized patient can be reported to the visitor. Therefore, even when the called hospitalized patient is not in the hospital room, the visitor can meet the hospitalized patient by going to the reported location.

In the above description, the location information of the patient mobile phone 10 is reported. However, without limitation thereto, a location information receiver capable of receiving location information transmitted from the IMES transmitter 16 may be carried by a hospitalized patient, and the location information of the location information receiver may be reported.

In this modification, the controller 8 has the mobile phone/hospitalized patient association table 74. However, the nurse call master device 7 may have the mobile phone/hospitalized patient association table 74, or another storage device may have the mobile phone/hospitalized patient association table 74.

Hereinafter, another nurse call system in an attempt to improve convenience for hospitalized patients will be described. Here, operation is performed such that, if something belonging to a hospitalized patient is lost (moved from a predetermined location) in the hospital room while the hospitalized patient is absent, notification of this fact is issued. The nurse call system that performs this operation is described as a nurse call system C.

Figure 16:
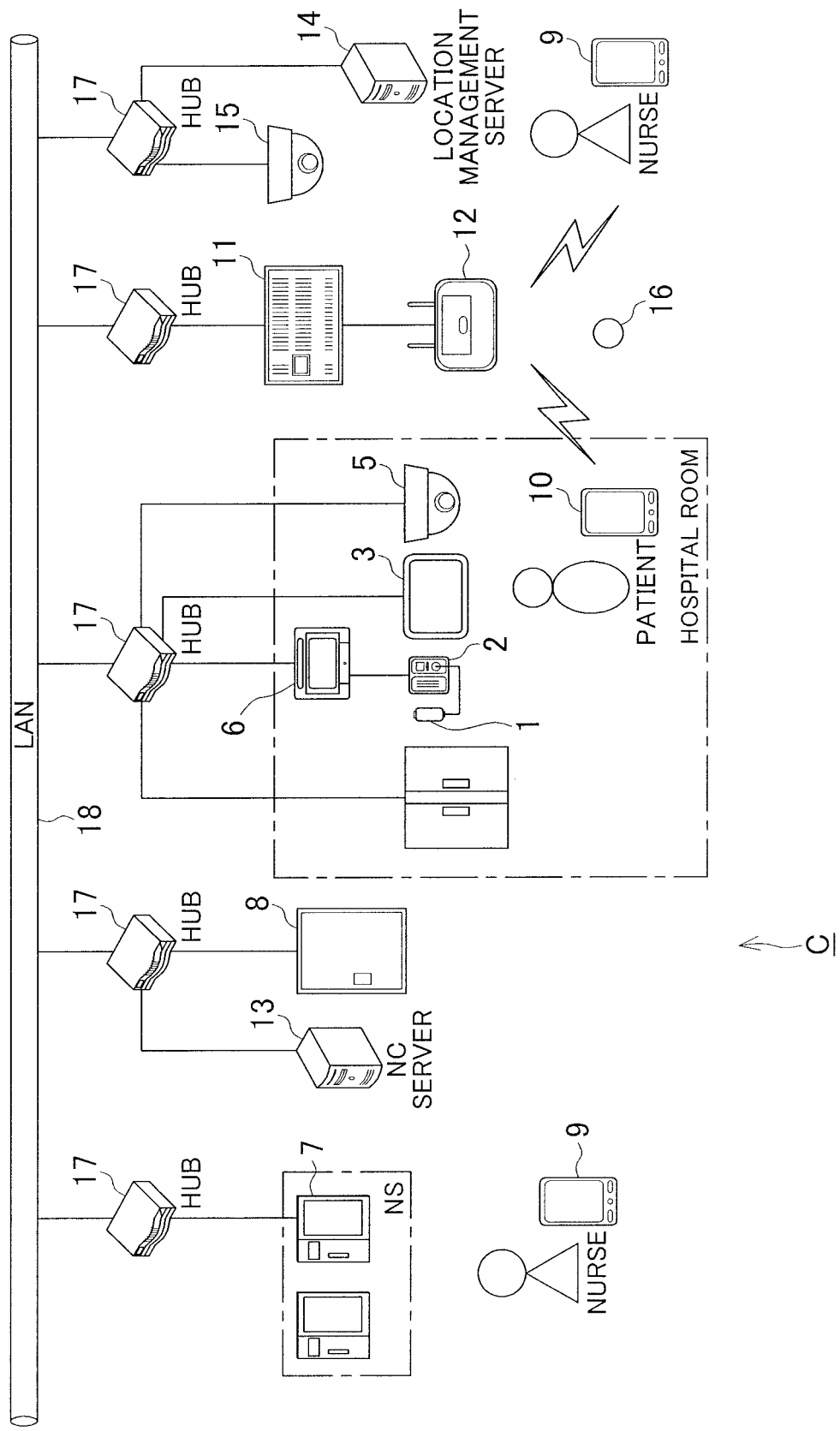
FIG. 16 shows another configuration of a nurse call system.

FIG. 16 shows the entire configuration of the nurse call system C. The nurse call system C has the same configuration as shown in FIG. 1 in the above embodiment, i.e., includes the nurse call slave device 1, the plate slave device 2, the bedside monitor 3, the hospital room camera 5, the corridor light 6, the nurse call master device 7, the controller 8, the nurse mobile phone 9, the patient mobile phone 10, the PBX 11, the base station 12, the nurse call server 13, the location management server 14, the common area camera 15, and the IMES transmitter 16.

Figure 17:
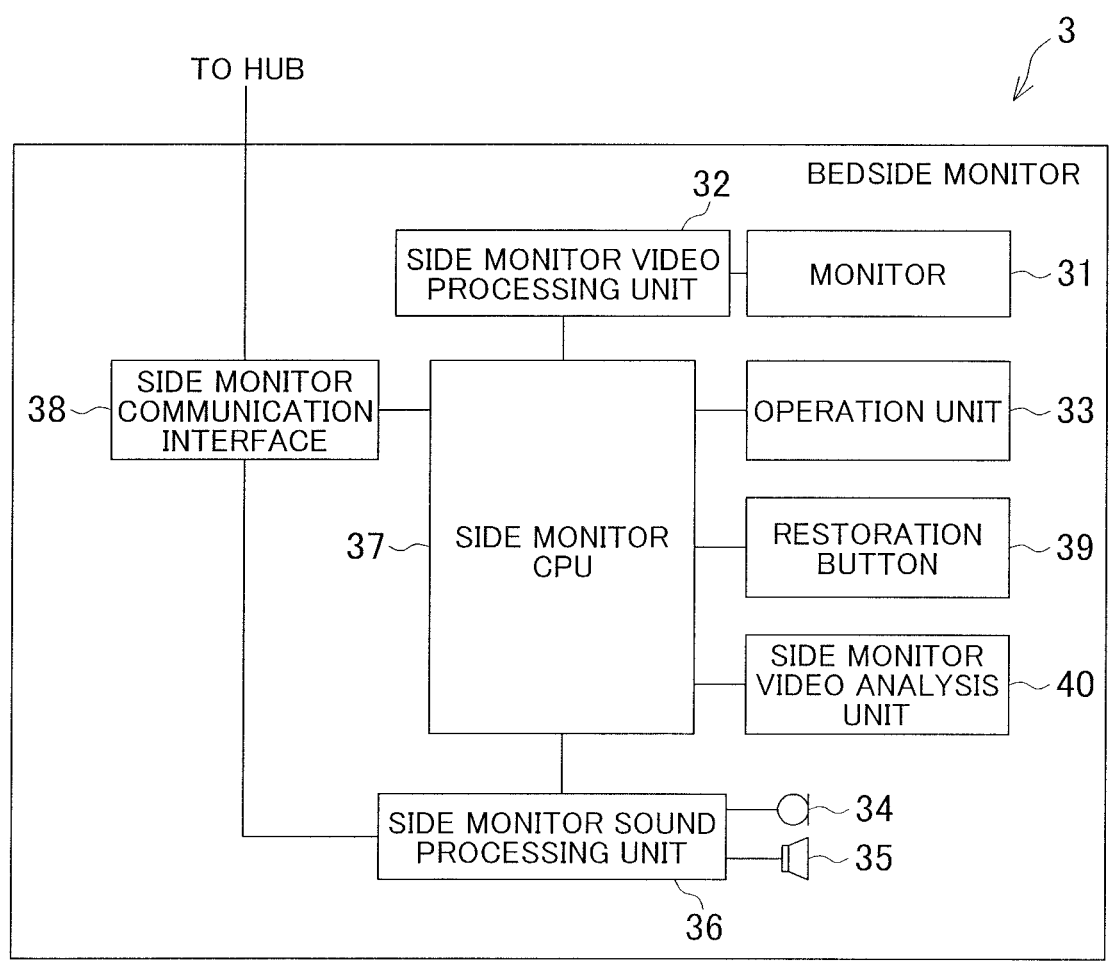
FIG. 17 is a function block diagram showing another configuration of a bedside monitor.

The bedside monitor 3 of the nurse call system C is configured as shown in FIG. 17, and includes, in addition to the components shown above in FIG. 11, a side monitor video analysis unit 40 capable of detecting change in the location of a predetermined object on the basis of a video taken by the hospital room camera 5. The corridor light 6 has the configuration as in the nurse call system B shown in FIG. 12.

Figure 18:
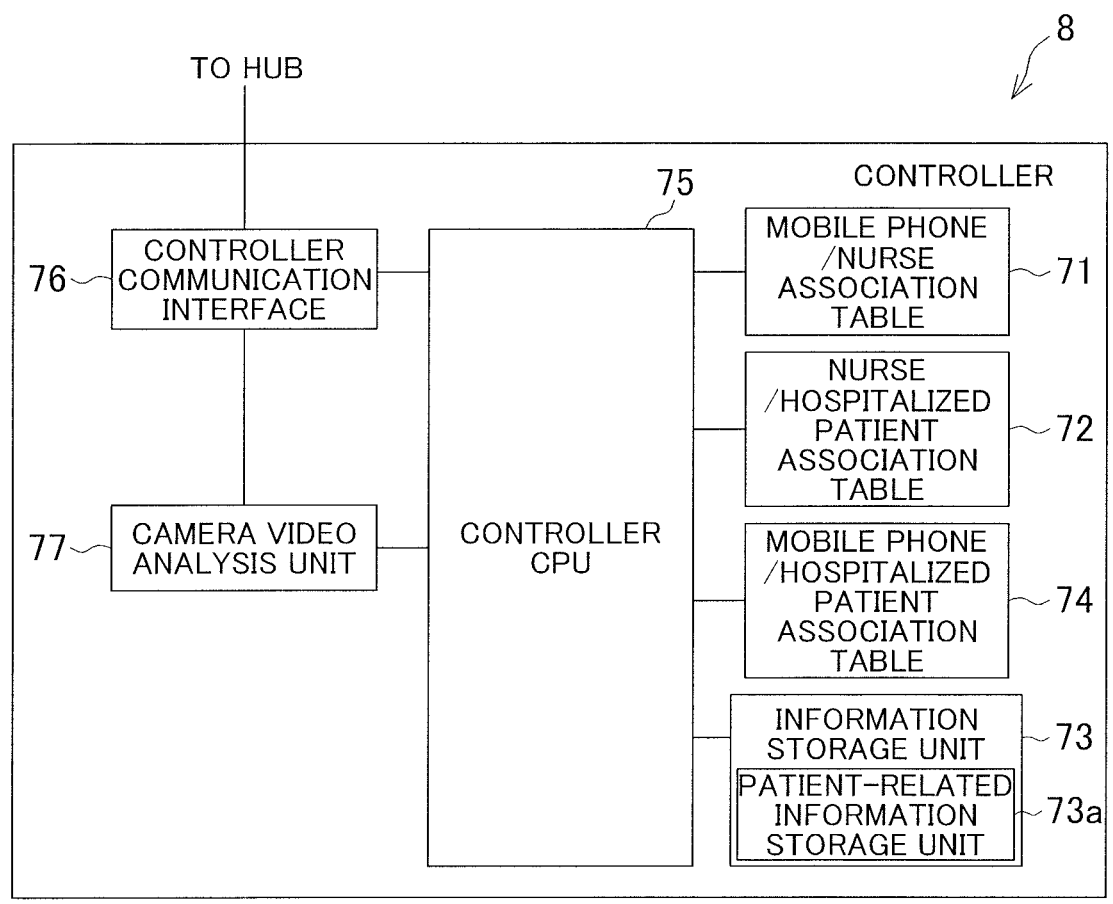
FIG. 18 is a function block diagram showing the configuration of a controller.

The controller 8 is configured as shown in FIG. 18, and includes, in addition to the components shown above in FIG. 6, a camera video analysis unit 77 for analyzing a video taken by the hospital room camera 5.

In the camera video analysis unit 77, a specific area is set in advance within the angle of view of the hospital room camera 5 for determination of bed leaving such that the specific area matches the bed that is an imaging target. The camera video analysis unit 77 determines whether bed leaving has occurred, by detecting a person moving out of the specific area.

Figure 19:
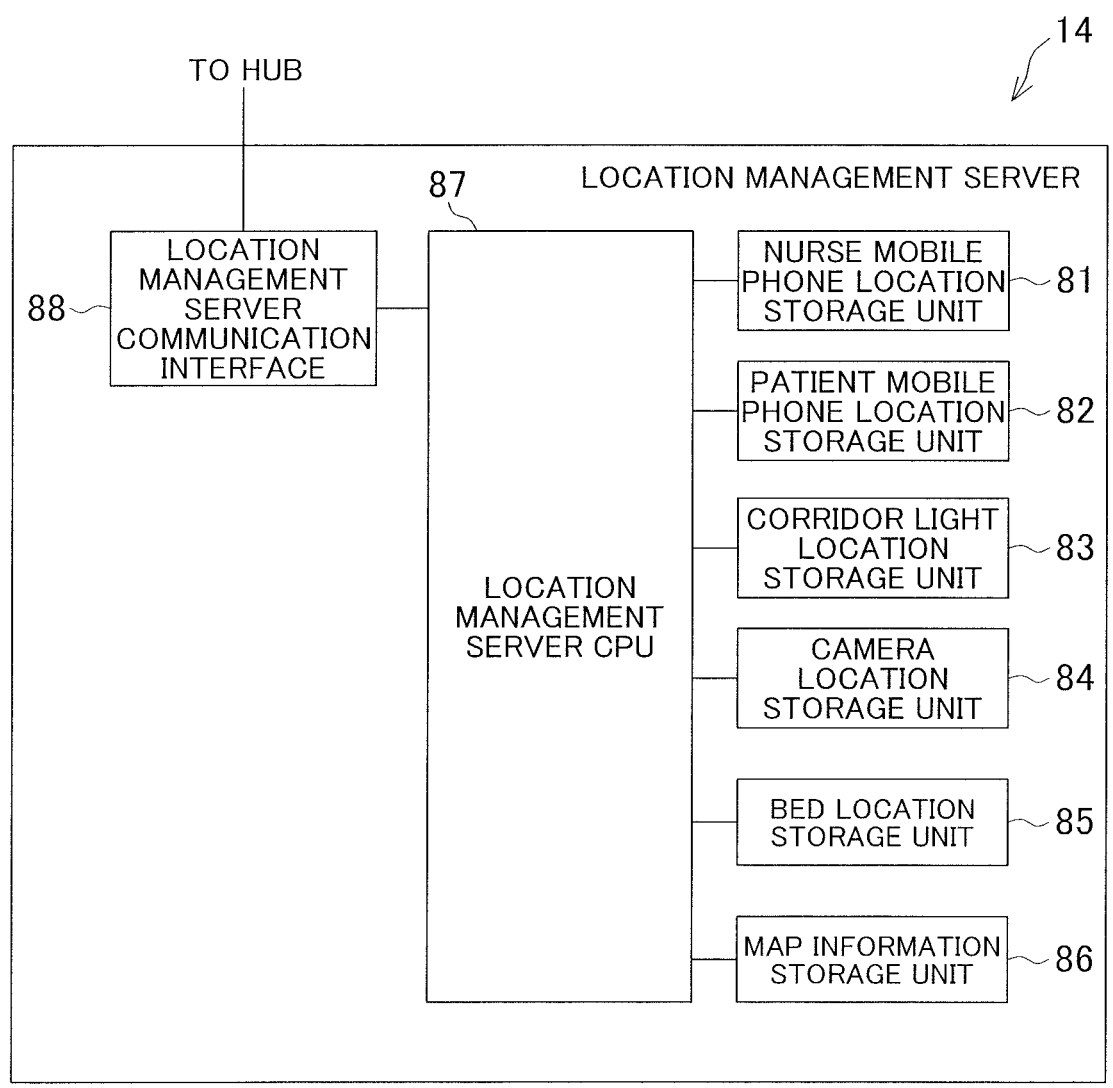
FIG. 19 is a function block diagram showing the configuration of a location management server.

The location management server 14 is configured as shown in FIG. 19, and includes, in addition to the components shown above in FIG. 8, a bed location storage unit 85 for storing the locations of the individual nurse call slave devices 1 in the hospital, and a map information storage unit (distance measurement unit) 86 for calculating a distance.

Operation of the nurse call system C configured as described above will be described below.

Here, a series of operations associated with registration of a monitoring target object based on operation on the bedside monitor 3 by a hospitalized patient will be described.

It is noted that, as described above, the location information of each nurse mobile phone 9 is regularly transmitted to the location management server 14, and data in the nurse mobile phone location storage unit 81 is rewritten and saved with the latest data through control by the location management server CPU 87. In addition, the hospital room camera 5 is operating at all times.

First, registration of a monitoring target object is performed through an operation on the bedside monitor 3 by a hospitalized patient.

Specifically, the registration is performed by a hospitalized patient touching a button for "registration of monitoring target object" in a function list displayed on the operation unit 33 of the monitor 31.

Figure 20:
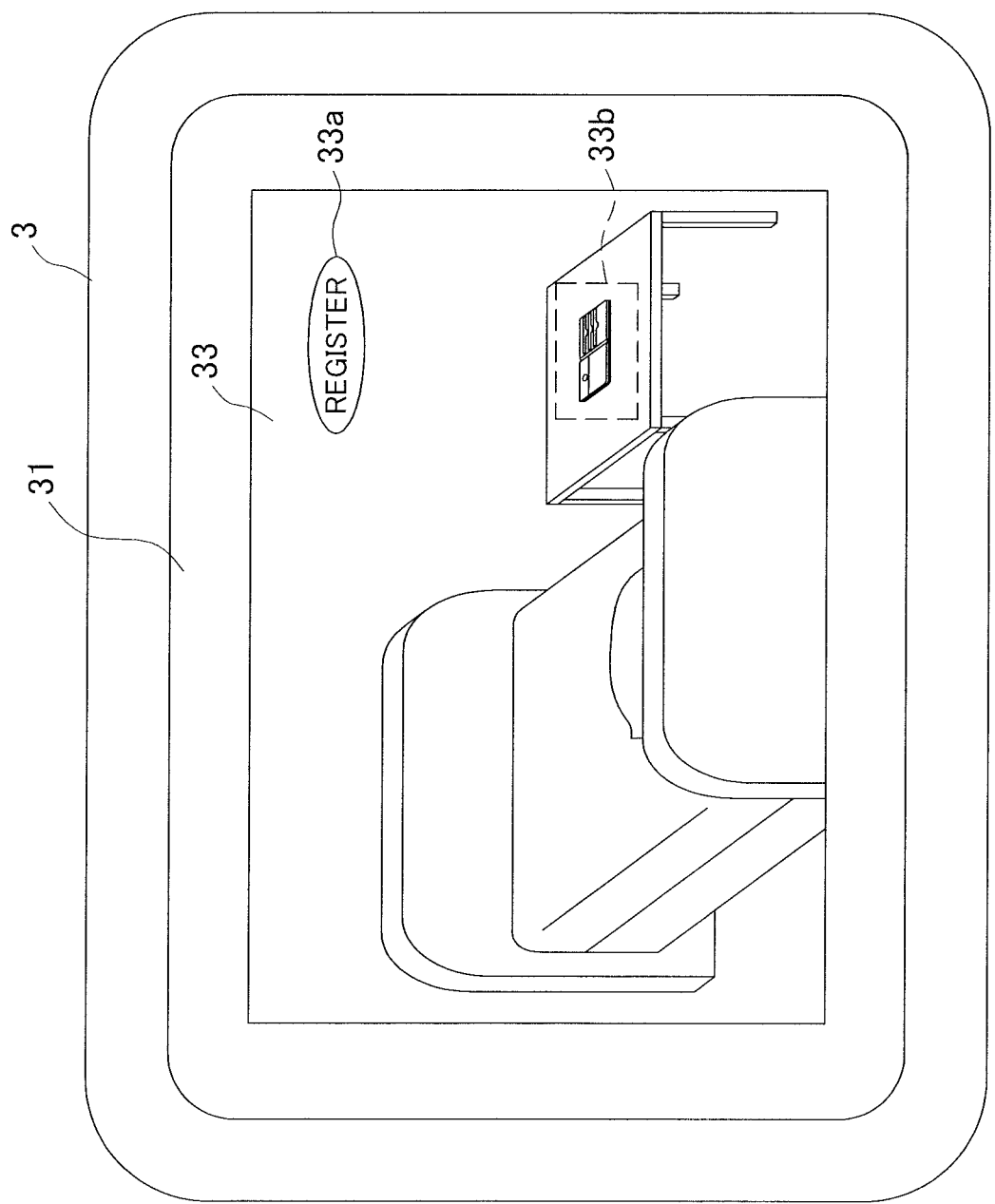
FIG. 20 shows an example of a screen displayed on the bedside monitor.

When the button for "registration of monitoring target object" is touched, the bedside monitor 3 under control by the side monitor CPU 37 starts to receive a video taken by the hospital room camera 5 and displays the received video taken by the hospital room camera 5 and a registration button 33a, on the operation unit 33 of the monitor 31, as shown in FIG. 20.

The hospitalized patient touches a part where an own object to be monitored is displayed on the displayed taken video, to enclose the part by a box 33b, and then touches the registration button 33a. Thus, registration of the monitoring target object is completed.

It is noted that, in the case where an own object desired to be monitored is not displayed as in the case where the own object desired to be monitored is in a drawer, the drawer part or the like which will be moved when the own object desired to be monitored is taken out may be touched.

When registration of the monitoring target object is completed as described above, the controller 8 starts detection for a bed-leaving state of the hospitalized patient from the video taken by the hospital room camera 5, using the camera video analysis unit 77.

When a bed-leaving state is detected by the camera video analysis unit 77, the controller 8 notifies the bedside monitor 3 of occurrence of bed leaving.

When the bedside monitor 3 has received the notification of occurrence of bed leaving from the controller 8, the bedside monitor 3 starts to monitor the monitoring target object by the side monitor video analysis unit 40. The monitoring of the monitoring target object by the side monitor video analysis unit 40 is performed by detecting change in the location of the monitoring target object on the basis of the video taken by the hospital room camera 5.

After monitoring of the monitoring target object is started, if change in the location of the monitoring target object is detected by the side monitor video analysis unit 40, the bedside monitor 3 transmits a location change detection signal indicating that change in the location of the monitoring target object is detected, to the controller 8.

The controller 8 that has received the location change detection signal confirms whether a bed-leaving state is being detected by the camera video analysis unit 77.

In the case where a bed-leaving state is being detected, the controller 8 reads information about the patient mobile phone 10 from the mobile phone/hospitalized patient association table 74, and transmits a location change signal indicating that the location of the monitoring target object has changed, to the patient mobile phone 10 of the hospitalized patient.

At the same time, the controller 8 reads the location of the nurse call slave device 1 of the hospitalized patient on the basis of the relationship information between the hospitalized patient and the nurse call slave device 1 (bed location), stored in the patient-related information storage unit 73a, and causes the location management server 14 to select the nurse mobile phone 9 that is nearest to the location of the nurse call slave device 1 on the basis of information in the nurse mobile phone location storage unit 81 and the map information storage unit 86.

The controller 8 also executes control for transmitting the location change signal to the nurse mobile phone 9 selected as described above.

The patient mobile phone 10 and the nurse mobile phone 9 that have received the location change signal each execute control on performing notification that the location of the monitoring target object has changed.

Specifically, the notification is performed by sound messages for reporting that the location of the monitoring target object has changed, e.g., the patient mobile phone 10 outputs a sound message "The location of the monitoring target object has changed. Please return and confirm.", and the nurse mobile phone 9 outputs a sound message "The location of the monitoring target object in room No. ZZ, bed No. YY, has changed. Please hurry to confirm".

As described above, the nurse call system C according to the present embodiment can notify a hospitalized patient and a nurse that the own object of the hospitalized patient has moved while the hospitalized patient is away from the bed. Therefore, after occurrence of a theft, the notified hospitalized patient or the notified nurse can immediately come to the site, and thus there is a possibility that the theft can be prevented. In addition, the location change signal can be transmitted to the nurse mobile phone 9 of the nurse who is near the bedside monitor at the transmission source of the location change signal, among the nurses. Therefore, after occurrence of a theft, the nurse can more immediately come to the hospital room, and thus there is a higher possibility that the theft can be prevented.

In the nurse call system C according to the present embodiment, a notification that the location of the monitoring target object has changed is given by using a sound message. However, without limitation thereto, a character message may be displayed in addition to output of the sound message, or only a character message may be displayed.

In the above configuration, the location change signal is transmitted to the patient mobile phone 10 and the nurse mobile phone 9 of the nurse who is near the nurse call slave device 1 of this hospitalized patient. However, without limitation thereto, the location change signal may be transmitted to at least one of the nurse call master device 7, the corridor light 6, the nurse mobile phone 9, and the patient mobile phone 10.

In the case of adopting a configuration in which the location change signal is transmitted to the corridor light 6, the corridor light 6 can perform the corresponding report by lighting up the call indication light 41 and outputting a sound message, e.g., "The location of the monitoring target object in the hospital room has changed. Please confirm." from the loudspeaker 53. In the case where the corridor light 6 has a liquid crystal monitor, the report may be displayed on the liquid crystal monitor by using a character message. The configuration in which the location change signal is transmitted to the corridor light 6 enables occurrence of a theft to be reported to every person who passes the corridor, and thus there is a possibility that the theft can be prevented.

In the case of adopting a configuration in which the location change signal is transmitted to the nurse mobile phone 9, the location change signal does not necessarily need to be transmitted to the nurse mobile phone 9 of the nurse who is near the nurse call slave device 1 of this hospitalized patient as in the present embodiment, but the location change signal may be transmitted to any of the nurse mobile phones 9.

On the other hand, in the case where a bed-leaving state is not detected, the controller 8 does not transmit a location change signal to the patient mobile phone 10 and the like. In the case where a bed-leaving state is not detected, it is considered that the hospitalized patient who has returned after once leaving the bed has moved the monitoring target object. Since this is not a theft, a report is not needed.

Thereafter, even if a bed-leaving state is detected, the controller 8 does not transmit a location change signal to the patient mobile phone 10 and the like, and meanwhile, executes control for displaying such a notification as to encourage re-registration of a monitoring target object, e.g., "Please re-register monitoring target object." on the monitor 31 of the bedside monitor 3.

Thus, in the case where a bed-leaving state is thereafter detected, it is considered that the hospitalized patient brings the monitoring target object to outside of the predetermined location, and therefore a report is not needed.

That is, according to the present embodiment, even in the case where the monitoring target object has moved, a notification is not performed unless that is a theft. Thus, the convenience is high.

In addition, according to the present embodiment, the hospitalized patient who has returned after bringing the monitoring target object to outside of the predetermined location can be encouraged to re-register a monitoring target object.

In the nurse call system C according to the present embodiment, presence/absence of a hospitalized patient is detected through detection of bed leaving of the hospitalized patient by the camera video analysis unit 77 of the controller 8. However, without limitation thereto, for example, presence/absence of a hospitalized patient may be detected by detecting a hospital room leaving state in which the hospitalized patient disappears from the hospital room, from location information of the patient mobile phone 10 on the basis of information in the patient mobile phone location storage unit 82 of the location management server 14.

After the monitoring target object is registered, when the controller 8 has received a hospital room leaving state detection signal indicating that a hospital room leaving state is detected from the location management server 14, the controller 8 executes control for notifying the bedside monitor 3 of occurrence of a hospital room leaving state.

When the bedside monitor 3 has received the notification of occurrence of a hospital room leaving state from the location management server 14, the bedside monitor 3 starts to monitor the monitoring target object by the side monitor video analysis unit 40.

The operation after monitoring of the monitoring target object is started is as described above.

A hospitalized patient may carry a location information receiver capable of receiving location information transmitted from each IMES transmitter 16, and thus presence/absence of the hospitalized patient may be detected by detecting a hospital room leaving state in which the hospitalized patient disappears from the hospital room, from the location information of the hospitalized patient.

In the nurse call system C according to the present embodiment, the bedside monitor 3 executes monitoring of a monitoring target object by the side monitor video analysis unit 40. However, the camera video analysis unit 77 of the controller 8 may execute monitoring of a monitoring target object.

On the other hand, the side monitor video analysis unit 40 may detect a bed-leaving state of a hospitalized patient.

Such a video analysis unit for executing monitoring of a monitoring target object or executing detection for a bed-leaving state of a hospitalized patient may be provided to the corridor light 6, the hospital room camera 5, or the like.

The bedside monitor 3, the hospital room camera 5, the controller 8, or the like may further include a storage unit for storing a video taken by the hospital room camera 5. With such a configuration, a video taken during monitoring can be recorded, and therefore, in the case where a theft has occurred, the video taken during monitoring can be confirmed later.

Further, such a storage unit may store videos taken by the surrounding common area cameras 15.

The controller 8 may be configured to, as well as transmitting a location change signal to the nurse mobile phone 9, etc., execute control for emitting an alarm sound from the loudspeaker 35 of the bedside monitor 3. Such a configuration can notify a person who attempts a theft that the person has been monitored, and thus there is a possibility that the theft is prevented.

The controller 8 may be configured to, as well as transmitting a location change signal to the nurse mobile phone 9 and the like, transmit videos taken by the hospital room camera 5 and the surrounding common area cameras 15 thereto. Such a configuration can enable confirmation of the behavior of a person who has committed a theft, by the nurse mobile phone 9 or the like.

As described above, the nurse call system C is only required to have a configuration in which, in the case where a monitoring target object is registered through the operation unit 33, when an absent state of the hospitalized patient is detected by a presence/absence detection device such as the camera video analysis unit 77, the bedside monitor 3 or the controller 8 executes control for starting monitoring of the monitoring target object by a video analysis device such as the side monitor video analysis unit 40, and then, when change in the location of the monitoring target object is detected by the video analysis device, control is executed so as to transmit a location change signal indicating that the location of the monitoring target object has changed, to at least one of the nurse call master device 7, the corridor light 6, the nurse mobile phone 9, and the patient mobile phone 10. The configurations other than the above are optional.

It is explicitly stated that all features disclosed in the description and/or the claims are intended to be disclosed separately and independently from each other for the purpose of original disclosure as well as for the purpose of restricting the claimed invention independent of the composition of the features in the embodiments and/or the claims. It is explicitly stated that all value ranges or indications of groups of entities disclose every possible intermediate value or intermediate entity for the purpose of original disclosure as well as for the purpose of restricting the claimed invention, in particular as limits of value ranges.

What is claimed is:

1. A nurse call system comprising:
    a nurse call slave device provided for each of beds in a hospital room, for a hospitalized patient to call a nurse;
    a nurse call master device provided at a nurse station, for answering a call from the nurse call slave device;
    a plate slave device which is provided near the bed in the hospital room and to which the nurse call slave device is connected;
    a controller configured to control speech and communication between devices; and
    a plurality of nurse mobile phones connected to the controller via a PBX having a mobile phone exchange connection function and a base station having a mobile phone wireless transmission/reception function, the nurse mobile phones being carried by nurses for answering a call from the nurse call slave device, wherein a plurality of patient mobile phones are carried by hospitalized patients and connected to the controller via the base station and the PBX as with the nurse mobile phones, a location information transmitter configured to wirelessly transmit a location signal is provided at an appropriate location in a hospital, and a location management server configured to manage location information about each patient mobile phone is provided, each patient mobile phone includes a location information communication unit configured to receive the location signal transmitted from the location information transmitter and transmit the location signal with an ID of the patient mobile phone added thereto, each patient mobile phone has a hospital room ID and a nurse call slave device ID registered therein for specifying the patient carrying the patient mobile phone, and is capable of performing a nurse call to transmit a call signal with the hospital room ID and the nurse call slave device ID added thereto, and when a nurse call operation is executed on the patient mobile phone, the controller acquires location information about the patient mobile phone from the location management server, generates a call signal including the location information, and transmits the call signal to the nurse call master device and at least one of the nurse mobile phones.

2. The nurse call system according to claim 1, wherein cameras are provided at appropriate locations in the hospital room and a common area in a hospital ward, the location management server includes a camera location storage unit configured to store the location of each camera, and a camera specifying unit configured to specify the camera that is nearest to the patient mobile phone, and when the nurse call operation is performed on the patient mobile phone, the controller acquires information about the camera that is nearest the patient mobile phone on which the nurse call operation is performed, from the location management server, and transmits a video taken by the camera, together with the call signal transmitted through the nurse call operation.

3. The nurse call system according to claim 2, wherein the location management server includes a corridor light location storage unit configured to store a location of each of corridor lights, and a corridor light specifying unit configured to specify the corridor light that is nearest the patient mobile phone, and when the nurse call operation is performed on the patient mobile phone, the controller acquires information about the corridor light that is nearest the patient mobile phone on which the nurse call operation is performed, from the location management server, and transmits a call occurrence signal to the corridor light, to cause the corridor light to perform a nurse call occurrence notification operation.

4. The nurse call system according to claim 3, wherein the corridor light includes a corridor light monitor configured to display patient information as an image, the controller transmits the call occurrence signal with hospital room number information and bed number information added thereto, the hospital room number information and the bed number information being read from information about the hospital room ID and the nurse call slave device ID included in the call signal transmitted from the patient mobile phone, and the corridor light that has received the call occurrence signal displays the hospital room number information and the bed number information on the corridor light monitor.

5. The nurse call system according to any one of claim 1, wherein a shop terminal configured to manage an order from the hospitalized patient is provided at a shop in the hospital, and the patient mobile phone has a function of accessing the shop terminal and ordering a commodity, and through an ordering operation, the hospital room ID and the nurse call slave device ID are transmitted together with information about a commodity ordered from the patient mobile phone, to the shop terminal, so as to allow an ordering source to be recognized on the shop terminal.

6. The nurse call system according to any one of claim 1, wherein the patient mobile phone has a function of accessing an accounting server configured to manage an expense charged to each hospitalized patient in the hospital, so as to be capable of acquiring information about an expense charged to the patient associated with the patient mobile phone, from the accounting server.

7. The nurse call system according to any one of claim 1, wherein the hospital room ID and the nurse call slave device ID registered on the patient mobile phone are registered by software for which a term of validity is set.

\* \* \* \* \*